US012656679B2

(12) United States Patent
Cui et al.

(10) Patent No.: US 12,656,679 B2
(45) Date of Patent: Jun. 16, 2026

(54) COMPOUNDS AND PHOTORESIST COMPOSITIONS INCLUDING THE SAME

(71) Applicant: ROHM AND HAAS ELECTRONIC MATERIALS LLC, Marlborough, MA (US)

(72) Inventors: Li Cui, Westborough, MA (US); Emad Aqad, Northborough, MA (US); Yinjie Cen, Shrewsbury, MA (US); Conner A. Hoelzel, Brookline, MA (US); James F. Cameron, Brookline, MA (US); Jong Keun Park, Shrewsbury, MA (US); Suzanne M. Coley, Mansfield, MA (US); Choong-Bong Lee, Westborough, MA (US)

(73) Assignee: DUPONT ELECTRONIC MATERIALS INTERNATIONAL, LLC, Marlborough, MA (US)

( * ) Notice: Subject to any disclaimer, the term of this patent is extended or adjusted under 35 U.S.C. 154(b) by 880 days.

(21) Appl. No.: 17/749,880

(22) Filed: May 20, 2022

(65) Prior Publication Data

US 2024/0019779 A1 Jan. 18, 2024

(51) Int. Cl.

| | |
|---|---|
| ***G03F 7/004*** | (2006.01) |
| ***C07C 69/78*** | (2006.01) |
| ***C07C 317/22*** | (2006.01) |

(52) U.S. Cl.

CPC ............ *G03F 7/0045* (2013.01); *C07C 69/78* (2013.01); *C07C 317/22* (2013.01); *C07C 2601/08* (2017.05); *C07C 2601/16* (2017.05)

(58) Field of Classification Search

None

See application file for complete search history.

(56) References Cited

U.S. PATENT DOCUMENTS

| | | | | |
|---|---|---|---|---|
| 4,189,323 | A | 2/1980 | Buhr | |
| 7,534,547 | B2 | 5/2009 | Hanabata et al. | |
| 7,736,834 | B2 * | 6/2010 | Miyasaka | G03F 7/42 430/311 |
| 8,431,325 | B2 | 4/2013 | Hashimoto et al. | |
| 10,421,708 | B2 | 9/2019 | Qian | |
| 2009/0004596 | A1 * | 1/2009 | Bucchignano | G03F 7/0392 430/296 |
| 2012/0100481 | A1 * | 4/2012 | Ito | G03F 7/0392 430/296 |
| 2018/0186723 | A1 * | 7/2018 | Qian | G03F 7/031 |
| 2020/0026188 | A1 * | 1/2020 | Maruyama | C08F 220/1818 |

FOREIGN PATENT DOCUMENTS

| | | | | |
|---|---|---|---|---|
| CN | 111440115 A | | 7/2020 | |
| JP | 2007248515 A | * | 9/2007 | |
| JP | 2009241418 A | | 10/2009 | |
| JP | 2011180304 A | | 9/2011 | |
| JP | 2012063728 A | | 3/2012 | |
| JP | 2013001811 A | | 1/2013 | |
| JP | 2018527418 A | | 9/2018 | |
| JP | 2020008640 A | | 1/2020 | |
| KR | 100768364 B1 | | 10/2007 | |
| WO | WO-2016076205 A1 | * | 5/2016 | C09B 69/103 |
| WO | WO-2018180049 A1 | * | 10/2018 | C08F 220/1807 |

OTHER PUBLICATIONS

WO2018180049 English Translation (Year: 2025).*
WO 2016076205 English Translation (Year: 2025).*
Translated Description of Konno (Year: 2016).*
Translated Description of Kazuyoshi (Year: 2007).*

* cited by examiner

*Primary Examiner* — Andrew Preston Traywick
(74) *Attorney, Agent, or Firm* — CANTOR COLBURN LLP

(57) ABSTRACT

A compound represented by Formula (1):

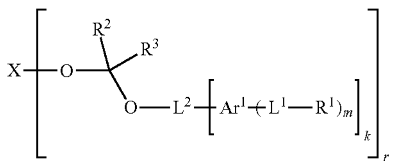

(1)

wherein X is a group having a valency of r; each $R^1$ is independently an organic group comprising an acid-labile group; m is an integer greater than or equal to 1; k is an integer from 1 to 5; and r is an integer from 2 to 10, wherein the compound is non-polymeric, and wherein $Ar^1$, $L^1$, $L^2$, $R^2$, and $R^3$ are as defined herein.

20 Claims, No Drawings

COMPOUNDS AND PHOTORESIST COMPOSITIONS INCLUDING THE SAME

FIELD

The present invention relates to cleavable compounds, photoresist compositions including such compounds, and pattern formation methods using such photoresist compositions. The invention finds particular applicability in lithographic applications in the semiconductor manufacturing industry.

BACKGROUND

Photoresist compositions are photosensitive materials used to transfer a pattern to one or more underlying layers, such as a metal, semiconductor, or dielectric layer disposed on a substrate. Positive-tone chemically amplified photoresist compositions are conventionally used for high-resolution processing. Such resist compositions typically include a polymer having acid-labile groups and a photoacid generator (PAG). A layer of the photoresist composition is pattern-wise exposed to activating radiation and the PAG generates an acid in the exposed regions. During post-exposure baking, the acid causes cleavage of the polymer's acid-labile groups. This creates a difference in solubility characteristics between exposed and unexposed regions of the photoresist layer in a developer solution. In a positive tone development (PTD) process, exposed regions of the photoresist layer become soluble in a developer, typically an aqueous base developer, and are removed from the substrate surface. Unexposed regions, which are insoluble in the developer, remain after development to form a positive relief image. The resulting relief image permits selective processing of the substrate.

To increase the integration density of semiconductor devices and allow for the formation of structures having dimensions in the nanometer (nm) range, photoresists and photolithography processing tools having high-resolution capabilities have been and continue to be developed. One approach to achieving nm-scale feature sizes in semiconductor devices is the use of activating radiation having a short wavelength, for example, 193 nm or less, for exposure of the photoresist layer. To further improve lithographic performance, immersion lithography tools have been developed to effectively increase the numerical aperture (NA) of the lens of the imaging device. This is accomplished by use of a relatively high refractive index fluid, typically water, between the last surface of the imaging device and the upper surface of the semiconductor wafer.

Deep-ultraviolet argon fluoride (ArF) excimer-laser immersion tools are currently pushing the boundaries of lithographic processing to the 16 nm and 14 nm device nodes with the use of multiple (double, triple, or higher order) patterning techniques. The use of multiple patterning, however, can be costly in terms of increased material usage and number of process steps required as compared with single step, directly imaged patterns. The need for photoresist compositions for next-generation (e.g., Extreme Ultraviolet, EUV) lithography, which use activating radiation having an extremely short wavelength of 13.5 nm, has thus become of increased importance for advanced device nodes. At the extreme feature sizes associated with these nodes, the performance requirements of photoresist compositions have become increasingly more stringent. Desired performance properties include, for example, high sensitivity to activating radiation, low unexposed film thickness loss, good contrast, high-resolving capability, and good line-width roughness (LWR).

Accordingly, there remains a continued need in the art for new compounds useful in photoresist compositions that may result in improved lithographic performance.

SUMMARY

Provided is a compound represented by Formula (1):

(1)

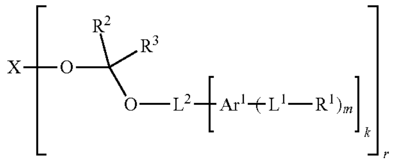

wherein, X is a group having a valency of r; each $L^1$ is independently a single bond or a divalent linking group; each $L^2$ is a single bond or a linking group; each $Ar^1$ is independently substituted or unsubstituted $C_{6-30}$ arylene or substituted or unsubstituted $C_{3-30}$ heteroarylene, wherein the substituted $C_{6-30}$ arylene and the substituted $C_{3-30}$ heteroarylene are each independently substituted with at least one of halogen, $C_{1-30}$ alkyl, $C_{1-30}$ alkoxy, $C_{4-30}$ cycloalkyl, $C_{3-30}$ heterocycloalkyl, $C_{2-30}$ alkenyl, $C_{2-30}$ alkynyl, $C_{6-30}$ aryl, $C_{7-30}$ arylalkyl, $C_{7-30}$ alkylaryl, $C_{6-30}$ aryloxy, $C_{3-30}$ heteroaryl, $C_{4-30}$ alkylheteroaryl, $C_{4-30}$ heteroarylalkyl, or $C_{3-30}$ heteroaryloxy; each $R^1$ is independently an organic group comprising an acid-labile group; $R^2$ and $R^3$ are each independently hydrogen, or substituted or unsubstituted $C_{1-30}$ alkyl; $R^2$ and $R^3$ together optionally form a ring via a single bond or a divalent linking group, wherein the ring is substituted or unsubstituted; m is an integer greater than or equal to 1; k is an integer from 1 to 5; and r is an integer from 2 to 10, and wherein the compound is non-polymeric.

Also provided is a coated substrate comprising (a) a substrate having one or more layers to be patterned on a surface thereof; and (b) a layer of the inventive compound disposed over the one or more layers to be patterned.

Another aspect provides a photoresist composition comprising the inventive compound and a solvent.

Also provided is a method for forming a pattern comprising applying a layer of the inventive compound on a substrate to provide a photoresist layer; pattern-wise exposing the photoresist layer to activating radiation to provide an exposed photoresist layer; and developing the exposed photoresist layer to provide a photoresist pattern.

Another aspect provides a method for forming a pattern comprising applying a layer of the photoresist composition on a substrate to provide a photoresist composition layer; pattern-wise exposing the photoresist composition layer to activating radiation to provide an exposed photoresist composition layer; and developing the exposed photoresist composition layer to provide a photoresist pattern.

DETAILED DESCRIPTION

Reference will now be made in detail to exemplary embodiments, examples of which are illustrated in the present description. In this regard, the present exemplary embodiments may have different forms and should not be construed as being limited to the descriptions set forth herein.

Accordingly, the exemplary embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

As used herein, the terms "a," "an," and "the" do not denote a limitation of quantity and are to be construed to cover both the singular and the plural, unless otherwise indicated herein or clearly contradicted by context. "Or" means "and/or" unless clearly indicated otherwise. The modifier "about" used in connection with a quantity is inclusive of the stated value and has the meaning dictated by the context (e.g., includes the degree of error associated with measurement of the particular quantity). All ranges disclosed herein are inclusive of the endpoints, and the endpoints are independently combinable with each other. The suffix "(s)" is intended to include both the singular and the plural of the term that it modifies, thereby including at least one of that term. "Optional" or "optionally" means that the subsequently described event or circumstance can or cannot occur, and that the description includes instances where the event occurs and instances where it does not. The terms "first," "second," and the like, herein do not denote an order, quantity, or importance, but rather are used to distinguish one element from another. When an element is referred to as being "on" another element, it may be directly in contact with the other element or intervening elements may be present therebetween. In contrast, when an element is referred to as being "directly on" another element, there are no intervening elements present. It is to be understood that the described components, elements, limitations, and/or features of aspects may be combined in any suitable manner in the various aspects.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, the term "hydrocarbon" refers to an organic compound or group having at least one carbon atom and at least one hydrogen atom; "alkyl" refers to a straight or branched chain saturated hydrocarbon group having the specified number of carbon atoms and having a valence of one; "alkylene" refers to an alkyl group having a valence of two; "hydroxyalkyl" refers to an alkyl group substituted with at least one hydroxyl group (—OH); "alkoxy" refers to "alkyl-O—"; "carboxyl" and "carboxylic acid group" refer to a group having the formula "—C(═O)—OH"; "cycloalkyl" refers to a monovalent group having one or more saturated rings in which all ring members are carbon; "cycloalkylene" refers to a cycloalkyl group having a valence of two; "alkenyl" refers to a straight or branched chain, monovalent hydrocarbon group having at least one carbon-carbon double bond; "alkenoxy" refers to "alkenyl-O—"; "alkenylene" refers to an alkenyl group having a valence of two; "cycloalkenyl" refers to a non-aromatic cyclic divalent hydrocarbon group having at least three carbon atoms, with at least one carbon-carbon double bond; "alkynyl" refers to a monovalent hydrocarbon group having at least one carbon-carbon triple bond; the term "aromatic group" refers to a monocyclic or polycyclic aromatic ring system that satisfies Huckel's Rule (4n+2 π electrons) and includes carbon atoms in the ring; the term "heteroaromatic group" refers to an aromatic group that includes one or more heteroatoms (e.g., 1-4 heteroatoms) selected from N, O, and S instead of a carbon atom in the ring; "aryl" refers to a monovalent monocyclic or polycyclic aromatic ring system where every ring member is carbon, and may include a group with an aromatic ring fused to at least one cycloalkyl or heterocycloalkyl ring; "arylene" refers to an aryl group having a valence of two; "alkylaryl" refers to an aryl group that has been substituted with an alkyl group; "arylalkyl" refers to an alkyl group that has been substituted with an aryl group; "aryloxy" refers to "aryl-O—"; and "arylthio" refers to "aryl-S—".

The prefix "hetero" means that the compound or group includes at least one member that is a heteroatom (e.g., 1, 2, 3, or 4 or more heteroatom(s)) instead of a carbon atom, wherein the heteroatom(s) is each independently N, O, S, Si, or P; "heteroatom-containing group" refers to a substituent group that includes at least one heteroatom; "heteroalkyl" refers to an alkyl group having at least one heteroatom instead of carbon.

As used herein, the term "(meth)acrylic" includes both acrylic and methacrylic species (i.e., acrylic and methacrylic monomers), and the term "(meth)acrylate" includes both acrylate and methacrylate species (i.e., acrylate and methacrylate monomers).

Each of the foregoing substituent groups optionally may be substituted unless expressly provided otherwise. The term "optionally substituted" refers to being substituted or unsubstituted. "Substituted" means that at least one hydrogen atom of the chemical structure or group is replaced with another terminal substituent group that is typically monovalent, provided that the designated atom's normal valence is not exceeded. When the substituent is oxo (i.e., O), then two geminal hydrogen atoms on the carbon atom are replaced with the terminal oxo group. It is further noted that the oxo group is bonded to carbon via a double bond to form a carbonyl (C═O), where the carbonyl group is represented herein as —C(O)—. Combinations of substituents or variables are permissible. Exemplary substituent groups that may be present on a "substituted" position include, but are not limited to, nitro (—$NO_2$), cyano (—CN; may also be referred to as "a nitrile group"), hydroxyl (—OH), oxo (O), amino (—$NH_2$), mono- or di-($C_{1-6}$)alkylamino, alkanoyl (such as a $C_{2-6}$ alkanoyl group such as acyl), formyl (—C(O)H), carboxylic acid or an alkali metal or ammonium salt thereof; esters (including acrylates, methacrylates, and lactones) such as $C_{2-6}$ alkyl esters (—C(O)O-alkyl or —OC(O)-alkyl) and $C_{7-13}$ aryl esters (—C(O)O-aryl or —OC(O)-aryl); amido (—C(O)$NR_2$ wherein R is hydrogen or $C_{1-6}$ alkyl), carboxamido (—$CH_2C(O)NR_2$ wherein R is hydrogen or $C_{1-6}$ alkyl), halogen, thiol (—SH), $C_{1-6}$ alkylthio (—S-alkyl), thiocyano (—SCN), $C_{1-6}$ alkyl, $C_{2-6}$ alkenyl, $C_{2-6}$ alkynyl, $C_{1-6}$ haloalkyl, $C_{1-9}$ alkoxy, $C_{1-6}$ haloalkoxy, $C_{3-12}$ cycloalkyl, $C_{5-18}$ cycloalkenyl, $C_{2-18}$ heterocycloalkenyl, $C_{6-12}$ aryl having at least one aromatic ring (e.g., phenyl, biphenyl, naphthyl, or the like, each ring either substituted or unsubstituted aromatic), $C_{7-19}$ arylalkyl having 1 to 3 separate or fused rings and from 6 to 18 ring carbon atoms, arylalkoxy having 1 to 3 separate or fused rings and from 6 to 18 ring carbon atoms, $C_{7-12}$ alkylaryl, $C_{3-12}$ heterocycloalkyl, $C_{3-12}$ heteroaryl, $C_{1-6}$ alkyl sulfonyl (—$S(O)_2$-alkyl), $C_{6-12}$ arylsulfonyl (—$S(O)_2$-aryl), or tosyl ($CH_3C_6H_4SO_2$—). When a group is substituted, the indicated number of carbon atoms is the total number of carbon atoms in the group, excluding those of any substituents. For example, the group —$CH_2CH_2CN$ is a cyano-substituted $C_2$ alkyl group.

The term "halogen" as used herein refers to a monovalent substituent that is fluorine (fluoro), chlorine (chloro), bromine (bromo), or iodine (iodo). The prefix "halo" means a group including one or more of a fluoro, chloro, bromo, or iodo substituent instead of at least one hydrogen atom. In some aspects, a combination of halo groups (e.g., bromo and fluoro) may be present. In other aspects, only fluoro groups may be present. For example, the term "haloalkyl" (e.g., a $C_{1-8}$ haloalkyl) as used herein refers to an alkyl group substituted with one or more halogens. As used herein, "substituted $C_1$0.8 haloalkyl" refers to a $C_{1-8}$ alkyl group substituted one or more halogens, and is further substituted with one or more other substituent groups that are not halogens. It is to be understood that substitution of a group with a halogen atom is not to be considered a heteroatom-containing group, because a halogen atom does not replace a carbon atom. Hence, an unsubstituted $C_{1-8}$ haloalkyl is not considered a heteroalkyl group.

As used herein, when a definition is not otherwise provided, a "divalent linking group" refers to a divalent group including one or more of —O—, —S—, —Te—, —Se—, —C(O)—, C(O)O—, —N(R')—, —C(O)N(R')—, —S(O)—, —$S(O)_2$—, —C(S)—, —C(Te)—, —C(Se)—, substituted or unsubstituted $C_{1-30}$ alkylene, substituted or unsubstituted $C_{3-30}$ cycloalkylene, substituted or unsubstituted $C_{3-30}$ heterocycloalkylene, substituted or unsubstituted $C_{6-30}$ arylene, substituted or unsubstituted $C_{3-30}$ heteroarylene, or a combination thereof, wherein each R' is independently hydrogen, substituted or unsubstituted $C_{1-20}$ alkyl, substituted or unsubstituted $C_{1-20}$ heteroalkyl, substituted or unsubstituted $C_{6-30}$ aryl, or substituted or unsubstituted $C_{3-30}$ heteroaryl. Typically, the divalent linking group includes one or more of —O—, —S—, —C(O)—, —N(R')—, —S(O)—, —$S(O)_2$—, substituted or unsubstituted $C_{1-30}$ alkylene, substituted or unsubstituted $C_{3-30}$ cycloalkylene, substituted or unsubstituted $C_{3-30}$ heterocycloalkylene, substituted or unsubstituted $C_{6-30}$ arylene, substituted or unsubstituted $C_{3-30}$ heteroarylene, or a combination thereof, wherein R' is hydrogen, substituted or unsubstituted $C_{1-20}$ alkyl, substituted or unsubstituted $C_{1-20}$ heteroalkyl, substituted or unsubstituted $C_{6-30}$ aryl, or substituted or unsubstituted $C_{3-30}$ heteroaryl. More typically, the divalent linking group includes at least one of —O—, —C(O)—, —C(O)O—, —N(R')—, —C(O)N(R')—, substituted or unsubstituted $C_{1-10}$ alkylene, substituted or unsubstituted $C_{3-10}$ cycloalkylene, substituted or unsubstituted $C_{3-10}$ heterocycloalkylene, substituted or unsubstituted $C_{6-10}$ arylene, substituted or unsubstituted $C_{3-10}$ heteroarylene, or a combination thereof, wherein R is hydrogen, substituted or unsubstituted $C_{1-10}$ alkyl, substituted or unsubstituted $C_{1-10}$ heteroalkyl, substituted or unsubstituted $C_{6-10}$ aryl, or substituted or unsubstituted $C_{3-10}$ heteroaryl.

Provided are inventive compounds that may be used in photolithography, for example in photoresist compositions. Photoresist compositions including the inventive compounds are remarkably able to achieve improved lithographic performance. The compounds are represented by Formula (1):

(1)

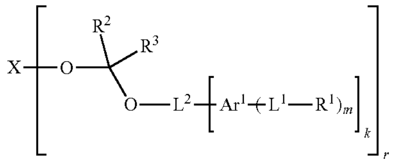

In Formula (1), X is a group having a valency of r. For example, X is a divalent group when r is 2, or X is a trivalent group when r is 3, or X is a tetravalent group when r is 4, or X is a pentavalent group when r is 5, or X is a hexavalent group when r is 6.

In Formula (1), each $R^1$ is independently an organic group comprising an acid-labile group. As used herein, an "acid-labile group" refers to a group having a bond that is cleavable by the action of an acid, optionally (and typically) with thermal treatment, resulting in formation of a polar group, such as a carboxylic acid group or an alcohol group. Suitable acid-labile groups include, for example: tertiary alkyl ester groups, secondary or tertiary aryl ester groups, secondary or tertiary ester groups having a combination of alkyl and aryl groups, tertiary alkoxy groups, acetal groups, or ketal groups. Acid-labile groups are also commonly referred to in the art as "acid-cleavable groups," "acid-cleavable protecting groups," "acid-labile protecting groups," "acid-leaving groups," "acid-decomposable groups," and "acid-sensitive groups."

In Formula (1), $R^2$ and $R^3$ are each independently hydrogen, or substituted or unsubstituted $C_{1-30}$ alkyl. Preferably, $R^2$ and $R^3$ may each independently be hydrogen, or substituted or unsubstituted $C_{1-10}$ alkyl, and typically $R^2$ and $R^3$ are each independently hydrogen, or substituted or unsubstituted $C_{1-6}$ alkyl. In some embodiments, $R^2$ is hydrogen and $R^3$ is substituted or unsubstituted $C_{1-6}$ alkyl. Each of $R^2$ and $R^3$ may optionally further comprise a divalent linking group as part of its structure.

$R^2$ and $R^3$ together optionally form a ring via a single bond or a divalent linking group, wherein the ring is substituted or unsubstituted.

In Formula (1), each $L^2$ is a single bond or a linking group. For example, each $L^2$ may be a linking group including one or more of substituted or unsubstituted $C_{1-30}$ alkylene, substituted or unsubstituted $C_{3-30}$ cycloalkylene, substituted or unsubstituted $C_{1-30}$ heterocycloalkylene, substituted or unsubstituted $C_{6-30}$ arylene, substituted or unsubstituted $C_{1-30}$ heteroarylene, —O—, —C(O)—, —C(O)O—, —C(O)$NR^{1a}$—, or —N($R^{1b}$)—, wherein $R^{1a}$ and $R^{1b}$ are each independently hydrogen or $C_{1-6}$ alkyl. When $L^2$ includes —O—, one or more other additional group should be present in $L^2$ so as not to form a peroxide (i.e., a peroxo —O—O—) with the adjacent acetal or ketal oxygen. Preferably, $L^2$ is one or more of substituted or unsubstituted $C_{1-10}$ alkylene, —O—, —C(O)—, —C(O)O—, —C(O)$NR^{1a}$—, or —N($R^{1b}$)—, and typically $L^2$ may be one or more of substituted or unsubstituted $C_{1-6}$ alkylene, —O—, or —C(O)—. In some aspects, $L^2$ may be a linking group including one or more of substituted or unsubstituted $C_{1-30}$ alkylene, substituted or unsubstituted $C_{3-30}$ cycloalkylene, substituted or unsubstituted $C_{1-30}$ heterocycloalkylene, substituted or unsubstituted $C_{6-30}$ arylene, substituted or unsubstituted $C_{1-30}$ heteroarylene, —C(O)—, —C(O)O—, —C(O)$NR^{1a}$—, or —N($R^{1b}$)—, wherein $L^2$ optionally further includes one or more groups of the formula —O—, and wherein $R^{1a}$ and $R^{1b}$ are each independently hydrogen or $C_{1-6}$ alkyl.

In some aspects, $L^2$ may be a single bond or a divalent linking group. In other aspects, $L^2$ may be a trivalent linking group, a tetravalent linking group, a pentavalent linking group, or a hexavalent linking group based on the variable k as disclosed hereinbelow.

In Formula (1), each $Ar^1$ is independently substituted or unsubstituted $C_{6-30}$ arylene or substituted or unsubstituted $C_{3-30}$ heteroarylene, wherein the substituted $C_{6-30}$ arylene and the substituted $C_{3-30}$ heteroarylene are each independently substituted with at least one of halogen, $C_{1-30}$ alkyl, $C_{1-30}$ alkoxy, $C_{4-30}$ cycloalkyl, $C_{1-30}$ heterocycloalkyl, $C_{2-30}$ alkenyl, $C_{2-30}$ alkynyl, $C_{6-30}$ aryl, $C_{7-30}$ arylalkyl, $C_{7-30}$ alkylaryl, $C_{6-30}$ aryloxy, $C_{3-30}$ heteroaryl, $C_{4-30}$ alkylheteroaryl, $C_{4-30}$ heteroarylalkyl, or $C_{3-30}$ heteroaryloxy. Preferably, $Ar^1$ is independently substituted or unsubstituted $C_{6-14}$ arylene or substituted or unsubstituted $C_{3-10}$ heteroarylene, wherein the substituted $C_{6-14}$ arylene and the substituted $C_{3-10}$ heteroarylene are each independently substituted with at least one of halogen, $C_{1-10}$ alkyl, $C_{1-10}$ alkoxy, $C_{6-30}$ aryl, or $C_{3-30}$ heteroaryl. Typically, $Ar^1$ is a phenylene group, which is optionally substituted with one or more halogen atoms, such as one or more iodine.

In Formula (1), each $L^1$ is independently a single bond or a divalent linking group. For example, each $L^1$ may be a divalent linking group including one or more of substituted or unsubstituted $C_{1-30}$ alkylene, substituted or unsubstituted $C_{3-30}$ cycloalkylene, substituted or unsubstituted $C_{1-30}$ heterocycloalkylene, substituted or unsubstituted $C_{6-30}$ arylene, substituted or unsubstituted $C_{1-30}$ heteroarylene, —O—, —C(O)—, —C(O)O—, —C(O)NR$^{1a}$—, or —N(R$^{1b}$)—, wherein $R^{1a}$ and $R^{1b}$ are each independently hydrogen or $C_{1-6}$ alkyl. Preferably, $L^1$ is a single bond or one or more of substituted or unsubstituted $C_1$0.10 alkylene, —O—, —C(O)—, —C(O)O—, —C(O)NR$^{1a}$—, or —N(R$^{1b}$)—, and typically $L^1$ may be a single bond or one or more of substituted or unsubstituted $C_{1-6}$ alkylene, —O—, —C(O)—, —C(O)O—, —C(O)NR$^{1a}$—, or —N(R$^{1b}$)—. In some aspects, each $L^1$ may be a divalent linking group including one or more of substituted or unsubstituted $C_{1-30}$ alkylene, substituted or unsubstituted $C_{3-30}$ cycloalkylene, substituted or unsubstituted $C_{1-30}$ heterocycloalkylene, substituted or unsubstituted $C_{6-30}$ arylene, substituted or unsubstituted $C_{1-30}$ heteroarylene, —C(O)—, —C(O)O—, —C(O)NR$^{1a}$—, or —N(R$^{1b}$)—, wherein each $L^1$ optionally further includes one or more groups of the formula —O—, and wherein $R^{1a}$ and $R^{1b}$ are each independently hydrogen or $C_{1-6}$ alkyl. When more than one $L^1$ is present, each $L^1$ may be the same or different.

In Formula (1), each $R^1$ is independently an organic group comprising an acid-labile group. Exemplary acid-labile groups include tertiary alkyl ester groups, secondary or tertiary aryl ester groups, secondary or tertiary ester groups having a combination of alkyl and aryl groups, tertiary alkoxy groups, acetal groups, or ketal groups. In some embodiments, the acid-labile group of one or more $R^1$ comprises an ester group. In some embodiments, the acid-labile group of one or more $R^1$ comprises an acetal group.

In some aspects, $R^1$ may have a structure represented by one of Formula (2a) or Formula (2b):

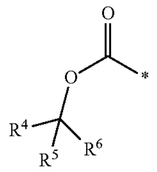

(2a)

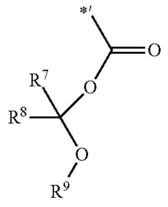

(2b)

In Formula (2a), R to R are each independently hydrogen, substituted or unsubstituted $C_{1-20}$ alkyl, substituted or unsubstituted $C_{3-20}$ cycloalkyl, substituted or unsubstituted $C_{3-20}$ heterocycloalkyl, substituted or unsubstituted $C_{2-20}$ alkenyl, substituted or unsubstituted $C_{3-20}$ cycloalkenyl, substituted or unsubstituted $C_{3-20}$ heterocycloalkenyl, substituted or unsubstituted $C_{6-20}$ aryl, or substituted or unsubstituted $C_{2-20}$ heteroaryl, provided that no more than one selected from $R^4$ to $R^6$ is hydrogen, and provided that if one of $R^4$ to $R^6$ is hydrogen, then at least one of the others from $R^4$ to $R^6$ is substituted or unsubstituted $C_{6-20}$ aryl or substituted or unsubstituted $C_{3-20}$ heteroaryl.

Each of $R^4$ to $R^6$ may optionally further include a divalent linking group as part of its structure. For example, each of $R^2$ to $R^4$ may further comprise as part of its structure one or more groups selected from —O—, —C(O)—, —C(O)O—, —S—, —S(O)$_2$—, —N(R$^{2a}$)—, or —C(O)N(R$^{2b}$)— wherein $R^{2a}$ and $R^{2b}$ are each independently hydrogen, substituted or unsubstituted $C_{1-20}$ alkyl, substituted or unsubstituted $C_{3-20}$ cycloalkyl, or substituted or unsubstituted $C_{3-20}$ heterocycloalkyl. Typically, $R^4$ to $R^6$ are each independently hydrogen, substituted or unsubstituted $C_{1-10}$ alkyl, substituted or unsubstituted $C_{3-8}$ cycloalkyl, or substituted or unsubstituted $C_{6-14}$ aryl.

In Formula (2b), $R^7$ and $R^8$ are each independently hydrogen, substituted or unsubstituted $C_{1-20}$ alkyl, substituted or unsubstituted $C_{3-20}$ cycloalkyl, substituted or unsubstituted $C_{3-20}$ heterocycloalkyl, substituted or unsubstituted $C_{6-20}$ aryl, or substituted or unsubstituted $C_{2-20}$ heteroaryl. Each of $R^7$ and $R^8$ may optionally further include a divalent linking group as part of its structure. For example, each of $R^7$ and R(may further comprise as part of its structure one or more groups selected from —O—, —C(O)—, —C(O)O—, —S—, —S(O)$_2$—, —N(R$^{2a}$)—, or —C(O)N(R$^{2b}$)—, wherein $R^{2a}$ and $R^{2b}$ are each independently hydrogen, substituted or unsubstituted $C_{1-20}$ alkyl, substituted or unsubstituted $C_{3-20}$ cycloalkyl, or substituted or unsubstituted $C_{3-20}$ heterocycloalkyl. Typically, $R^7$ and $R^8$ are each independently hydrogen, or substituted or unsubstituted $C_{1-10}$ alkyl.

In Formula (2b), $R^9$ is substituted or unsubstituted $C_{1-20}$ alkyl, substituted or unsubstituted $C_{3-20}$ cycloalkyl, substituted or unsubstituted $C_{3-20}$ heterocycloalkyl, substituted or unsubstituted $C_{6-20}$ aryl, or substituted or unsubstituted $C_{3-20}$ heteroaryl. $R^9$ optionally may further comprise a divalent linking group as part of its structure. Typically, $R^9$ may be substituted or unsubstituted $C_{1-10}$ alkyl, substituted or unsubstituted $C_{3-8}$ cycloalkyl, or substituted or unsubstituted $C_{6-14}$ aryl.

In Formula (2a), any two of $R^4$ to $R^6$ together optionally may form a ring via a single bond or a divalent linking group, wherein the ring is substituted or unsubstituted. In Formula (2b), $R^7$ and $R^8$ together optionally may form a ring via a single bond or a divalent linking group, wherein the ring is substituted or unsubstituted. In Formula (2a), any one or more of $R^7$ or $R^8$ together with $R^9$ optionally may form a ring via a single bond or a divalent linking group, wherein the ring is substituted or unsubstituted.

In Formulae (2a) and (2b), * and *' each indicate a binding site to $L^1$. It is to be understood that when $L^1$ is a single bond, the corresponding * or *' indicates a binding site to $Ar^1$.

In Formula (1), m is an integer greater than or equal to 1, and represents the number of groups defined by the moiety $-(L^1-R^1)$ that are connected to $Ar^1$. In some aspects, m is preferably an integer from 1 to 5, or an integer from 1 to 4, or an integer from 1 to 3, or 1 or 2. Typically, m is an integer from 1 to 3. It is to be understood that when m is 2, $Ar^1$ is a trivalent group, and when m is 3, $Ar^1$ is a tetravalent group, and when m is 4, $Ar^1$ is a pentavalent group, and when m is 5, $Ar^1$ is a hexavalent group.

In Formula (1), k is an integer from 1 to 5, and represents the number of groups defined by the moiety $—Ar^1-(L^1-R^1)_m$ that are connected to $L^2$. In some aspects, k is preferably an integer from 1 to 4, or an integer from 1 to 3, or 1 or 2. Preferably, k is an integer from 1 to 3. It is to be understood that when k is 2, $L^2$ is a trivalent group, and when k is 3, $L^2$ is a tetravalent group, and when k is 4, $L^2$ is a pentavalent group, and when k is 5, $L^2$ is a hexavalent group.

In Formula (1), r is an integer from 2 to 10, and represents the number of groups defined by the moiety $—O—C(R^2)(R^3)—O-L^2-[Ar^1-(L-R)_m]k$. In some aspects, r is preferably an integer from 2 to 4, or 2 or 3. Preferably, r is 2. In some embodiments, each subunit represented by the integer r is the same.

In some embodiments, m is an integer from 1 to 3; k is 1; and r is 2.

In some embodiments, in Formula (1), the group defined by the moiety $—O-L^2-[Ar-(L-R')_m]k$ may be represented by Formula (3a):

(3a)

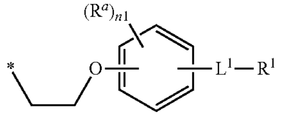

In Formula (3a), L is a single bond or one or more of substituted or unsubstituted $C_{1-10}$ alkylene, —O—, —C(O)—, —C(O)O—, $—C(O)NR^{1a}—$, or $—N(R^{1b})—$, and typically $L^1$ may be a single bond or one or more of substituted or unsubstituted $C_{1-6}$ alkylene, —O—, —C(O)—, —C(O)O—, $—C(O)NR^{1a}—$, or $—N(R^{1b})—$, wherein $R^{1a}$ and $R^{1b}$ are each independently hydrogen or $C_{1-6}$ alkyl.

In Formula (3a), $R^1$ is an organic group comprising an acid-labile group, as defined herein.

Exemplary groups for $R^1$ include the structures represented by one of Formula (2a) or Formula (2b).

In Formula (3a), each $R^a$ is halogen, $C_{1-10}$ alkyl, $C_{1-10}$ alkoxy, $C_{6-14}$ aryl, or $C_{3-30}$ heteroaryl. In some embodiments, $R^a$ may be iodine.

In Formula (3a), n1 is an integer from 0 to 4. Preferably, n1 is an integer from 0 to 2, or 0 or 1.

For example, in Formula (1), the group defined by the moiety $—O-L^2-[Ar^1-(L^1-R^1)_m]_k$ may be represented by Formula (3b):

(3b)

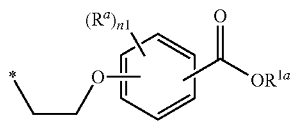

In Formula (3b), $R^{1a}$ is substituted or unsubstituted tertiary $C_{4-20}$ alkyl group, substituted or unsubstituted tertiary $C_{4-20}$ cycloalkyl group, or substituted or unsubstituted tertiary $C_{9-20}$ arylalkyl group. Preferably, $R^{1a}$ may be substituted or unsubstituted tertiary $C_{4-10}$ alkyl group, substituted or unsubstituted tertiary $C_{4-10}$ cycloalkyl group, or substituted or unsubstituted tertiary $C_{9-19}$ arylalkyl group.

In Formula (3b), each $R^a$ is halogen, $C_{1-10}$ alkyl, $C_{1-10}$ alkoxy, $C_{6-14}$ aryl, or $C_{3-30}$ heteroaryl. In some embodiments, $R^a$ may be iodine.

In Formula (3a), n1 is an integer from 0 to 4. Preferably, n1 is an integer from 0 to 2, or 0 or 1.

In some embodiments, X may include an aromatic group or a heteroaromatic group. For example, X may be represented by one of Formulae (4) to (9):

(4)

$*—Ar^2—*'$ (5)

$*—Ar^2—O—Ar^3—*'$ (6)

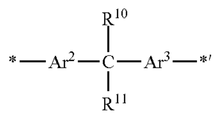

(7)

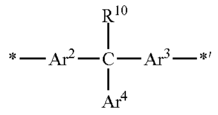

(8)

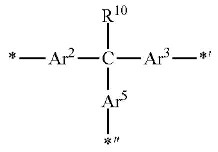

(9)

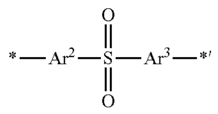

In Formulae (4) to (9), $Ar^2$, $Ar^3$, and $Ar^5$ are each independently substituted or unsubstituted $C_{6-30}$ arylene or substituted or unsubstituted $C_{3-30}$ heteroarylene. Preferably, $Ar^2$, $Ar^3$, and $Ar^5$ may each independently be substituted or unsubstituted $C_{6-14}$ arylene or substituted or unsubstituted $C_{3-20}$ heteroarylene, and typically $Ar^2$, $Ar^3$, and $Ar^5$ are each independently substituted or unsubstituted phenylene. In some aspects, $Ar^2$, $Ar^3$, and $Ar^5$ may each independently be substituted with 1 to 4 iodine atoms. For example, $Ar^2$, $Ar^3$, and $Ar^5$ may each independently be substituted with 1 to 3 iodine atoms, or 1 or 2 iodine atoms, or 1 iodine atom.

In Formula (7), $Ar^4$ is substituted or unsubstituted $C_{6-30}$ aryl or substituted or unsubstituted $C_{3-30}$ heteroaryl. Preferably, $Ar^4$ may be substituted or unsubstituted $C_{6-14}$ aryl or substituted or unsubstituted $C_{3-20}$ heteroaryl, and typically $Ar^4$ is substituted or unsubstituted phenylene. In some aspects, $Ar^4$ may be substituted with 1 to 4 iodine atoms. For example, $Ar^4$ may be substituted with 1 to 3 iodine atoms, or 1 or 2 iodine atoms, or 1 iodine atom.

In Formulae (6) to (8), $R^{10}$ and $R^{11}$ are each independently hydrogen, substituted or unsubstituted $C_{1-30}$ alkyl, substituted or unsubstituted $C_{3-30}$ cycloalkyl, substituted or unsubstituted $C_{1-30}$ heterocycloalkyl, substituted or unsubstituted $C_{6-30}$ aryl, substituted or unsubstituted $C_{7-30}$ arylalkyl, substituted or unsubstituted $C_{7-30}$ alkylaryl, substituted or unsubstituted $C_{6-30}$ aryloxy, substituted or unsubstituted $C_{3-30}$ heteroaryl, substituted or unsubstituted $C_{4-30}$ alkylheteroaryl, substituted or unsubstituted $C_{4-30}$ heteroarylalkyl, or substituted or unsubstituted $C_{3-30}$ heteroaryloxy. Preferably, $R^{10}$ and $R^{11}$ may each independently be substituted or unsubstituted $C_{1-10}$ alkyl, substituted or unsubstituted $C_{3-8}$ cycloalkyl, substituted or unsubstituted $C_{6-14}$ aryl, or substituted or unsubstituted $C_{3-20}$ heteroaryl.

In Formulae (4) to (9), * and *' each indicates a point of attachment to a respective adjacent oxygen atom. In Formula (8) *" indicates a point of attachment to a respective adjacent oxygen atom.

In some aspects, X may be represented by one of Formulae (4a) to (9a):

(4a)

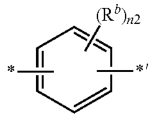

(5a)

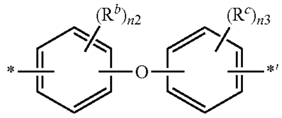

(6a)

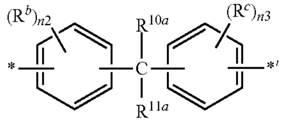

(7a)

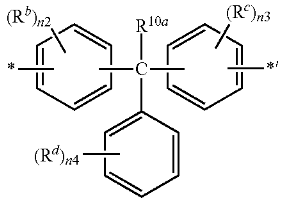

(8a)

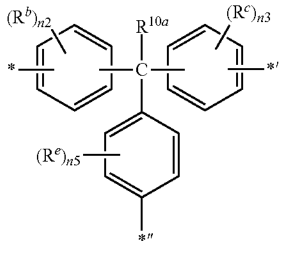

-continued (9a)

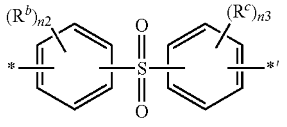

In Formulae (4a) to (9a), each $R^b$, $R^c$, $R^d$, and $R^e$ is independently halogen, $C_{1-30}$ alkyl, $C_{1-30}$ alkoxy, $C_{4-30}$ cycloalkyl, $C_{3-30}$ heterocycloalkyl, $C_{2-30}$ alkenyl, $C_{2-30}$ alkynyl, $C_{6-30}$ aryl, $C_{7-30}$ arylalkyl, $C_7$-30 alkylaryl, $C_{6-30}$ aryloxy, $C_{3-30}$ heteroaryl, $C_{4-30}$ alkylheteroaryl, $C_{4-30}$ heteroarylalkyl, or $C_{3-30}$ heteroaryloxy. Preferably, each $R^b$, $R^c$, and $R^d$ is independently halogen, $C_{1-10}$ alkyl, $C_{1-10}$ alkoxy, $C_{4-20}$ cycloalkyl, $C_{3-20}$ heterocycloalkyl, $C_{2-20}$ alkenyl, $C_{2-20}$ alkynyl, $C_{6-14}$ aryl, $C_{7-15}$ arylalkyl, $C_{7-15}$ alkylaryl, $C_{6-14}$ aryloxy, $C_{3-20}$ heteroaryl, $C_{4-20}$ alkylheteroaryl, $C_{4-20}$ heteroarylalkyl, or $C_{3-30}$ heteroaryloxy.

In Formulae (6a), (7a), and (8a), $R^{1a}$ is hydrogen, substituted or unsubstituted $C_{1-30}$ alkyl, substituted or unsubstituted $C_{3-30}$ cycloalkyl, substituted or unsubstituted $C_{1-30}$ heterocycloalkyl, substituted or unsubstituted $C_{6-30}$ aryl, substituted or unsubstituted $C_{7-30}$ arylalkyl, substituted or unsubstituted $C_{7-30}$ alkylaryl, substituted or unsubstituted $C_{6-30}$ aryloxy, substituted or unsubstituted $C_{3-30}$ heteroaryl, substituted or unsubstituted $C_{4-30}$ alkylheteroaryl, substituted or unsubstituted $C_{4-30}$ heteroarylalkyl, or substituted or unsubstituted $C_{3-30}$ heteroaryloxy. Preferably, $R^{10a}$ may be substituted or unsubstituted $C_{1-10}$ alkyl, substituted or unsubstituted $C_{3-5}$ cycloalkyl, substituted or unsubstituted $C_{6-14}$ aryl, or substituted or unsubstituted $C_{3-20}$ heteroaryl.

In Formulae (6a), $R^{10a}$ is hydrogen, substituted or unsubstituted $C_{1-30}$ alkyl, substituted or unsubstituted $C_{3-30}$ cycloalkyl, substituted or unsubstituted $C_{1-30}$ heterocycloalkyl, substituted or unsubstituted $C_{6-30}$ aryl, substituted or unsubstituted $C_{7-30}$ arylalkyl, substituted or unsubstituted $C_{7-30}$ alkylaryl, substituted or unsubstituted $C_{6-30}$ aryloxy, substituted or unsubstituted $C_{3-30}$ heteroaryl, substituted or unsubstituted $C_{4-30}$ alkylheteroaryl, substituted or unsubstituted $C_{4-30}$ heteroarylalkyl, or substituted or unsubstituted $C_{3-30}$ heteroaryloxy. Preferably, $R^{10a}$ may be substituted or unsubstituted $C_{1-10}$ alkyl, substituted or unsubstituted $C_{3-5}$ cycloalkyl, substituted or unsubstituted $C_{6-14}$ aryl, or substituted or unsubstituted $C_{3-20}$ heteroaryl.

In Formulae (4a) to (9a), n2, n3, and n5 are each independently an integer from 0 to 4. Preferably, n2 and n3 may each independently be an integer from 1 to 3, or 1 or 2, or 1.

In Formula (7a), n4 is an integer from 0 to 5. Preferably, n4 may be an integer from 1 to 4, or from 1 or 3, or 1 or 2.

In Formulae (4a) to (9a), * and *' each indicates a point of attachment to a respective adjacent oxygen atom. In Formula (8a), *" indicates a point of attachment to a respective adjacent oxygen atom.

The compounds of Formula (1) are non-polymeric. For example, the compounds of Formula (1) are not in a polymerized repeating unit of a polymer or an oligomer. It is to be understood that non-polymeric also means the compounds of Formula (1) are not in a polymer-bound form.

In some embodiments, the compound comprises one or more iodine atoms. For example, the compound may include 1 iodine atom, 2 iodine atoms, 3 iodine atoms, 4 iodine atoms, 5 iodine atoms, 6 iodine atoms, or 7 or more iodine atoms. In some aspects, the compound may include from 2 to 6 iodine atoms, or from 2 to 4 iodine atoms.

Exemplary compounds of Formula (1) include the following:
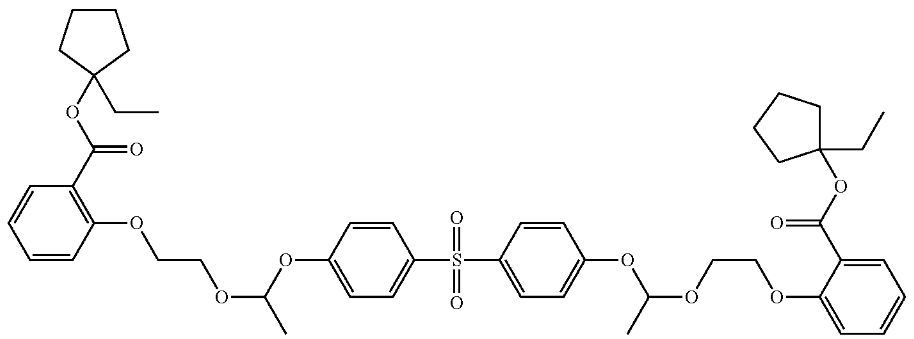
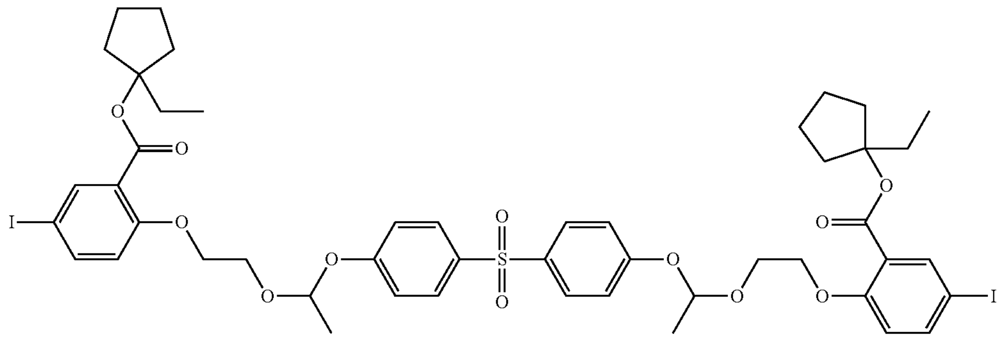
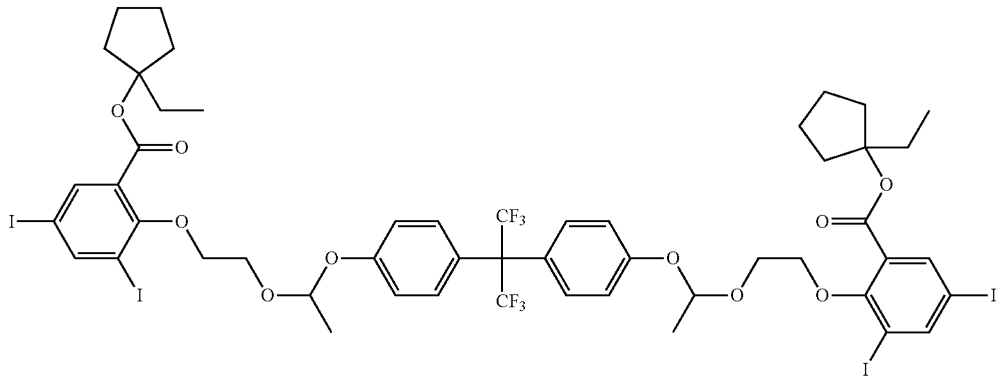
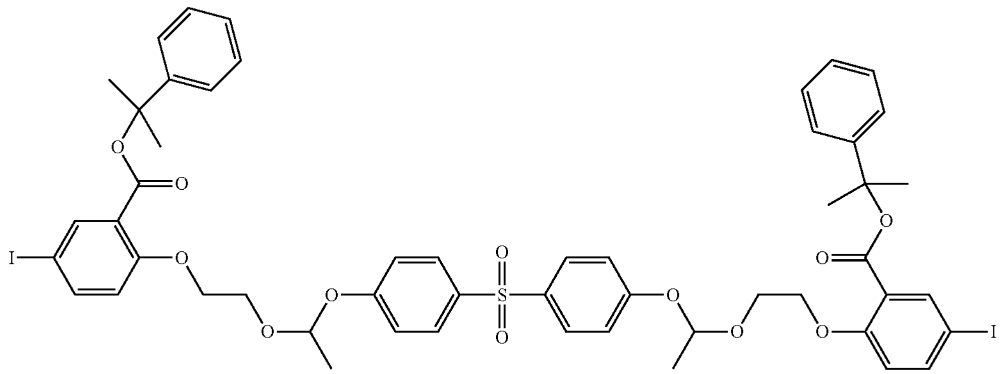

-continued

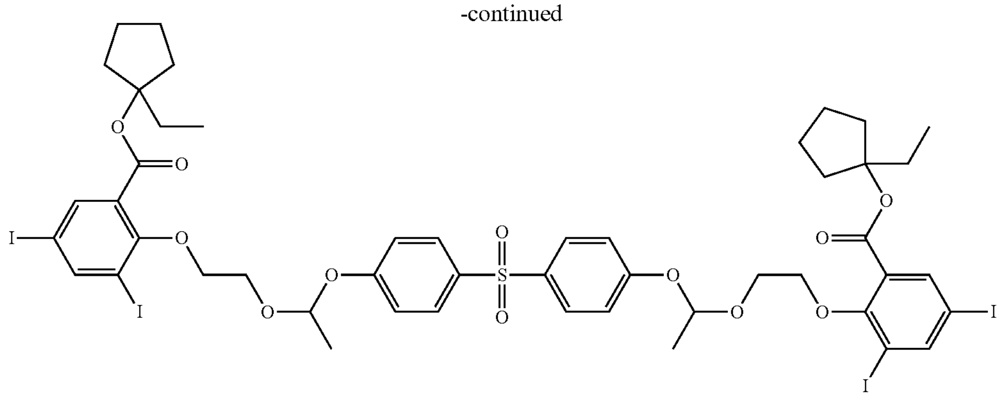

The compound of Formula (1) may have a formula weight from 100 to 15,000 grams per mole (g/mol), or from 300 to 3,000 g/mol, or from 400 to 3,000 g/mol, or from 800 to 2,000-g/mol.

The present invention further relates to photoresist compositions that include the inventive compound and a solvent, and may contain additional, optional components. Typically, the photoresist composition will further include a polymer, a photoacid generator (PAG), or a combination thereof.

The inventive compound may be present in the photoresist composition in an amount, for example, from 0.01 to 100 weight percent (wt %) based on total solids of the photoresist composition. The inventive compound may be used in the photoresist composition, for example, as an additive in a minor amount based on total solids, or as a matrix material in a major amount based on total solids of the photoresist composition. When used as an additive, the compound is typically included in the photoresist composition in an amount from 0.01 to 50 wt %, more typically from 0.01 to 20 wt %, from 0.01 to 10 wt %, or from 0.1 to 6 wt %, or from 0.5 to 5 wt %, based on total solids of the photoresist composition.

When used as a major solid component, the compound is typically included in the photoresist composition in an amount from greater than 50 to 100 wt %, from 70 to 100 wt %, or from 70 to 95 wt %, based on total solids of the photoresist composition. It will be understood that "total solids" includes the inventive compound and other non-solvent components of the photoresist composition.

The photoresist composition may further include a polymer having one or more repeating units. The repeating units may be, for example, one or more units for purposes of adjusting properties of the photoresist composition, such as etch rate and solubility. Exemplary repeating units may include those derived from one or more of (meth)acrylate, vinyl aromatic, vinyl ether, vinyl ketone, and/or vinyl ester monomers.

In some aspects, upon exposure with incident radiation, the inventive compound and optional polymer may undergo chain scission of the polymeric backbone along with scission of any acid-labile pendant groups. In some embodiments, the polymer does not include an acid-labile group.

In some embodiments, the polymer may be acid-sensitive, for example the polymer may include a repeating unit including an acid-labile group.

For example, the repeating unit including the acid-labile group may be derived from one or more monomers of Formulae (10) to (14):

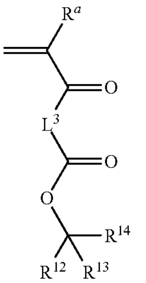

(10)

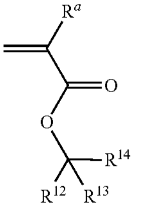

(11)

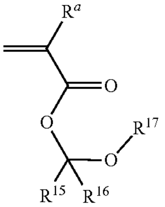

(12)

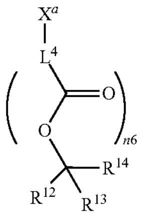

(13)

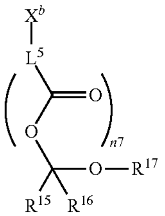

(14)

In Formulae (10) to (12), each $R^a$ is independently hydrogen, fluorine, cyano, or substituted or unsubstituted $C_{1-10}$ alkyl. Preferably, each $R^a$ is independently hydrogen, fluorine, or substituted or unsubstituted $C_{1-5}$ alkyl, typically methyl.

In Formula (10), $L^3$ is a divalent linking group. For example, $L^3$ may include 1 to 10 carbon atoms and at least one heteroatom. In a typical example, $L^1$ may be $—OCH_2—$, $—OCH_2CH_2O—$, or $—N(R^{10a})—$ wherein $R^{10a}$ is hydrogen or $C_{1-6}$ alkyl.

In Formulae (10), (11), and (13), $R^{12}$ to $R^{14}$ are each independently hydrogen, substituted or unsubstituted $C_{1-20}$ alkyl, substituted or unsubstituted $C_{3-20}$ cycloalkyl, substituted or unsubstituted $C_{3-20}$ heterocycloalkyl, substituted or unsubstituted $C_{2-20}$ alkenyl, substituted or unsubstituted $C_{3-20}$ cycloalkenyl, substituted or unsubstituted $C_{3-20}$ heterocycloalkenyl, substituted or unsubstituted $C_{6-20}$ aryl, or substituted or unsubstituted $C_{3-20}$ heteroaryl, provided that no more than one of $R^{12}$ to $R^{14}$ may be hydrogen, and provided that if one of $R^{12}$ to $R^{14}$ is hydrogen, then at least one of the others from $R^{12}$ to $R^{14}$ is substituted or unsubstituted $C_{6-20}$ aryl or substituted or unsubstituted $C_{3-20}$ heteroaryl. Preferably, $R^{15}$ to $R^{14}$ are each independently substituted or unsubstituted $C_{1-6}$ alkyl or substituted or unsubstituted $C_{3-10}$ cycloalkyl. Each of $R^{12}$ to $R^{14}$ may optionally further comprise a divalent linking group as part of their structure.

For example, any one or more of $R^{12}$ to $R^{14}$ may be independently a group of the formula $—CH_2C(O)CH_{(3-n)}Y_n$, or $—CH_2C(O)OCH_{(3-n)}Y_n$, where each Y is independently substituted or unsubstituted $C_{3-10}$ heterocycloalkyl and n is 1 or 2. For example, each Y may be independently substituted or unsubstituted $C_{3-10}$ heterocycloalkyl including a group of the formula $—O(C^{a1})(C^{a2})O—$, wherein $C^{a1}$ and $C^{a2}$ are each independently hydrogen or substituted or unsubstituted alkyl, and where $C^{a1}$ and $C^{a2}$ together optionally form a ring.

Any two of $R^{12}$ to $R^{14}$ together optionally may form a ring, which may further include a divalent linking group as part of its structure, and wherein the ring may be substituted or unsubstituted.

In Formulae (12) and (14), $R^{15}$ and $R^{16}$ each independently may be hydrogen, substituted or unsubstituted $C_{1-20}$ alkyl, substituted or unsubstituted $C_{3-20}$ cycloalkyl, substituted or unsubstituted $C_{3-20}$ heterocycloalkyl, substituted or unsubstituted $C_{6-20}$ aryl, or substituted or unsubstituted $C_{3-20}$ heteroaryl; and $R^{17}$ is substituted or unsubstituted $C_{1-20}$ alkyl, substituted or unsubstituted $C_{3-20}$ cycloalkyl, or substituted or unsubstituted $C_{3-20}$ heterocycloalkyl. Preferably, $R^{15}$ and $R^{16}$ each independently may be hydrogen, substituted or unsubstituted $C_{1-20}$ alkyl, substituted or unsubstituted $C_{3-20}$ cycloalkyl, or substituted or unsubstituted $C_{3-20}$ heterocycloalkyl. Each of $R^{15}$ and $R^{16}$ may optionally further comprise a divalent linking group as part of their structure.

Optionally, $R^{15}$ and $R^{16}$ together may form a ring, which may further include a divalent linking group as part of its structure, wherein the ring group may be substituted or unsubstituted.

Optionally, any one or more of $R^{15}$ or $R^{16}$ together with $R^{17}$ may form a ring, which may further include a divalent linking group as part of its structure, wherein the ring group may be substituted or unsubstituted In Formulae (13) and (14), $X^a$ and $X^b$ are each independently a polymerizable group comprising an ethylenically unsaturated double bond, preferably (meth)acrylate or $C_2$ alkenyl.

In Formulae (13) and (14), $L^4$ and $L^5$ are each independently a single bond or a divalent linking group, provided that $L^4$ is not a single bond when $X^a$ is $C_2$ alkenyl and that $L^5$ is not a single bond when $X^b$ is $C_2$ alkenyl. Preferably, $L^4$ and $L^5$ are each independently substituted or unsubstituted $C_{6-30}$ arylene or substituted or unsubstituted $C_{6-30}$ cycloalkylene. In Formulae (7) and (8), n1 is 0 or 1 and n2 is 0 or 1. It is to be understood that when n1 is 0, the $L^4$ group is connected directly to the oxygen atom. It is to be understood that when n2 is 0, the $L^5$ group is connected directly to the oxygen atom.

In some aspects, each of $R^{12}$ to $R^{17}$ optionally may further include as part of their structure one or more divalent linking groups selected from —O—, —C(O)—, —C(O)O—, —S—, $—S(O)_2—$, —N(R')—, or —C(O)N(R')—, wherein R' may be hydrogen, substituted or unsubstituted $C_{1-20}$ alkyl, substituted or unsubstituted $C_{3-20}$ cycloalkyl, or substituted or unsubstituted $C_{3-20}$ heterocycloalkyl.

In some aspects, in a repeating unit comprising an acid-labile group, the acid-labile group may be a tertiary alkyl ester. For example, a repeating unit comprising a tertiary alkyl ester group may be derived from one or more monomers of Formulae (10), (11), or (14), wherein none of $R^{12}$ to $R^{14}$ is hydrogen, and n1 is 1. In one or more embodiments, the polymer further comprises a second repeating unit comprising a tertiary alkyl ester group.

Exemplary monomers of Formula (10) include one or more of the following:

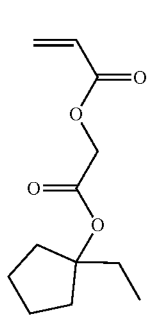

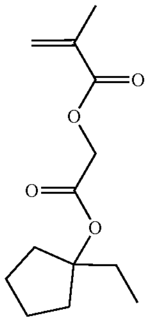

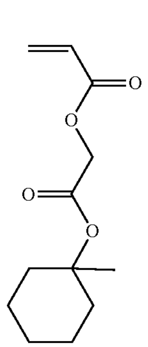

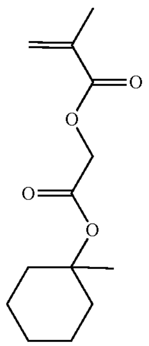

-continued
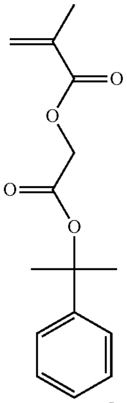
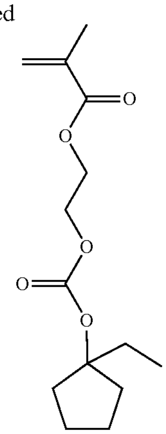
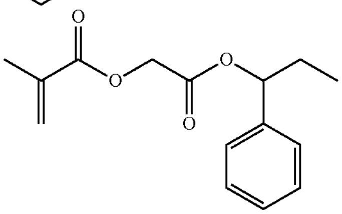
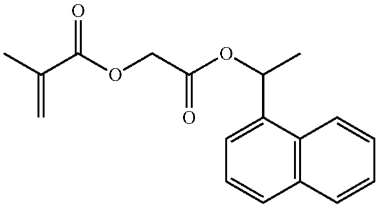
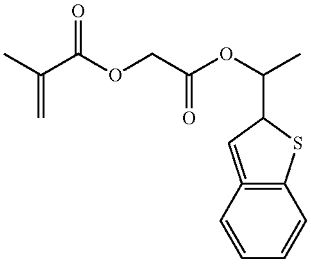
Exemplary monomers of Formula (11) include one or more of the following:
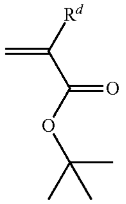
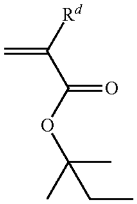
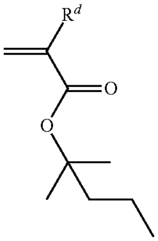
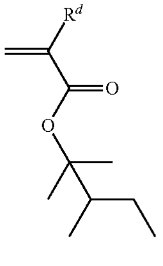
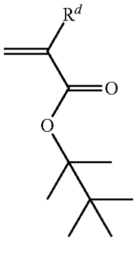
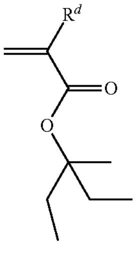
-continued
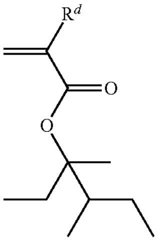
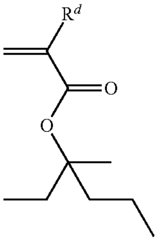
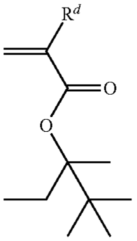
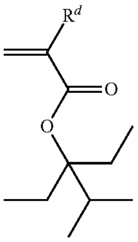
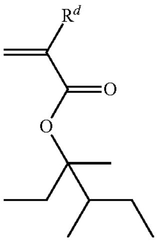
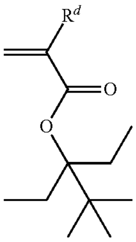
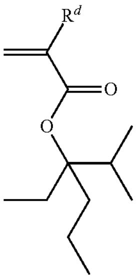
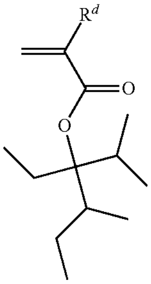
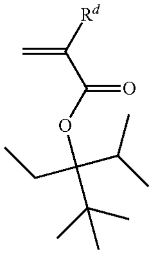
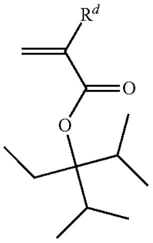
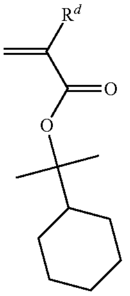
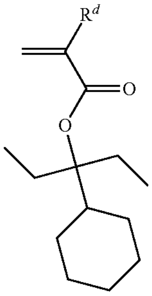
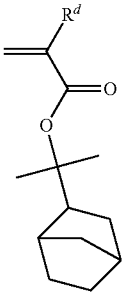
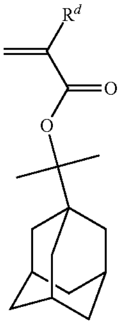
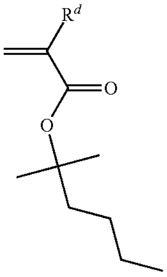
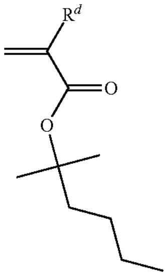

-continued

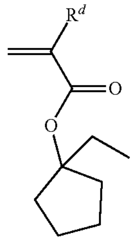
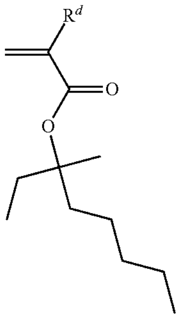
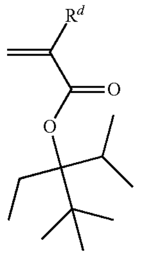
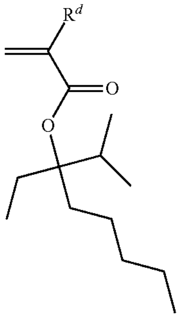
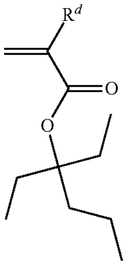
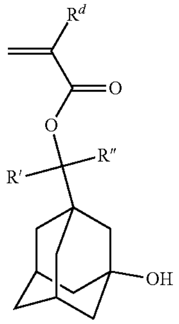
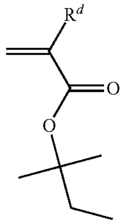
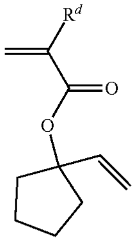
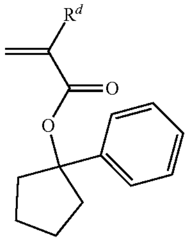
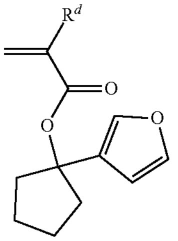
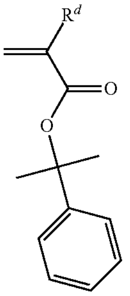
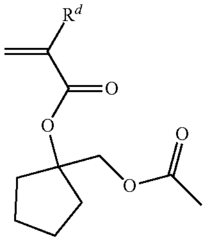
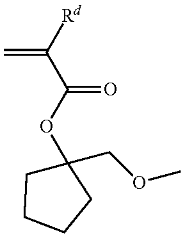
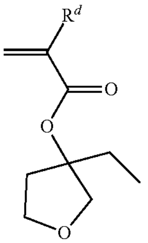
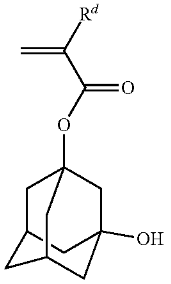

-continued

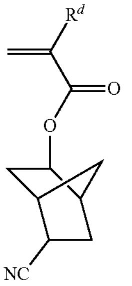
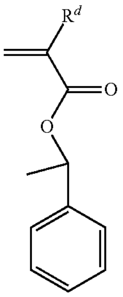
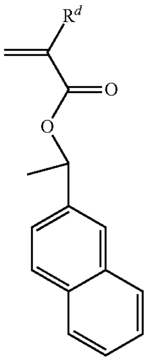
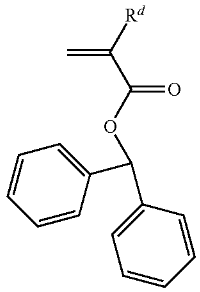
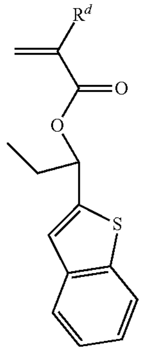
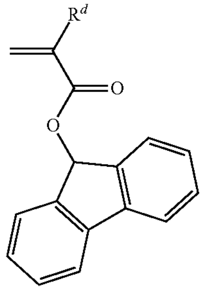

wherein $R^d$ is as defined herein for $R^a$ in Formula (11); and R' and $R^{15}$ are each independently substituted or unsubstituted $C_{1-20}$ alkyl, substituted or unsubstituted $C_{3-20}$ cycloalkyl, substituted or unsubstituted $C_{3-20}$ heterocycloalkyl, substituted or unsubstituted $C_{2-20}$ alkenyl, substituted or unsubstituted $C_{3-20}$ cycloalkenyl, substituted or unsubstituted $C_{3-20}$ heterocycloalkenyl, substituted or unsubstituted $C_{6-20}$ aryl, or substituted or unsubstituted $C_{3-20}$ heteroaryl.

Exemplary monomers of Formula (12) include one or more of the following:

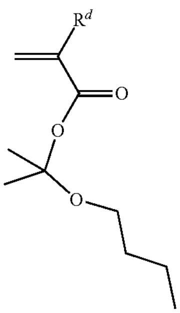
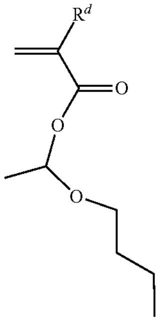

-continued
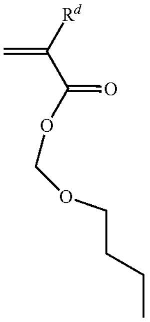
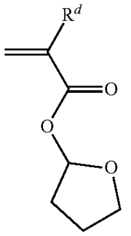
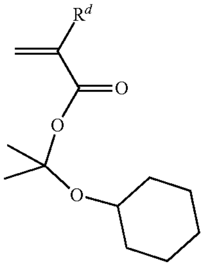
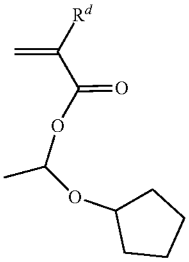
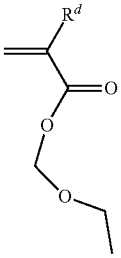
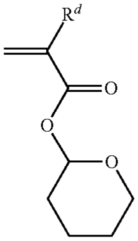
wherein $R^d$ is as defined above for $R^a$.
Exemplary monomers of Formula (13) include one or more of the following:
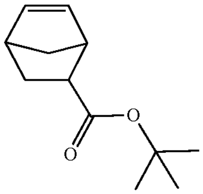
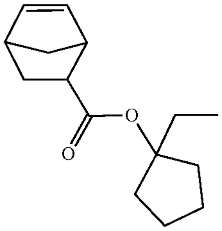
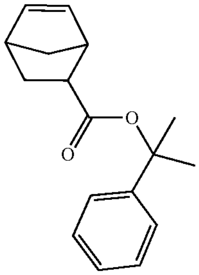
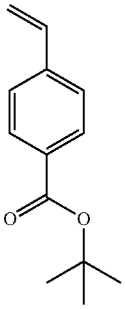
-continued
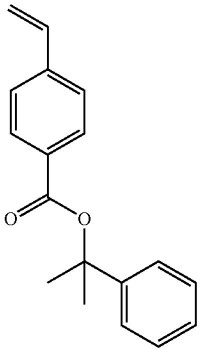
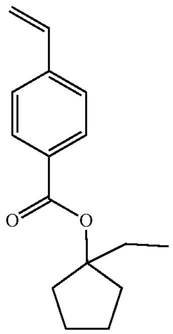
Exemplary monomers of Formula (14) include one or more of the following:
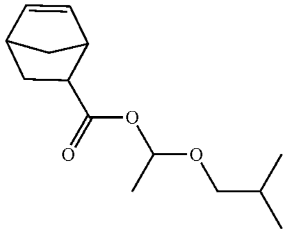
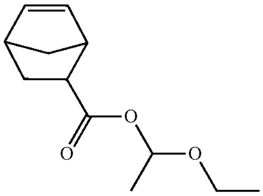
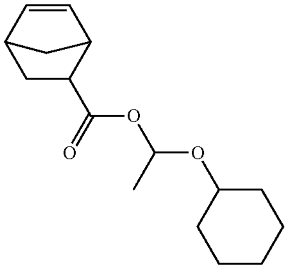
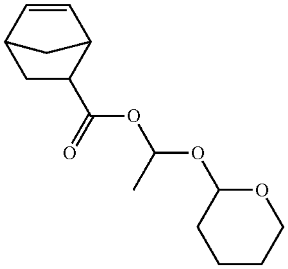

-continued
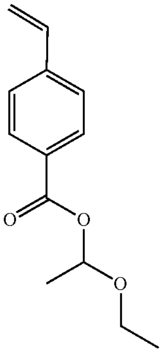
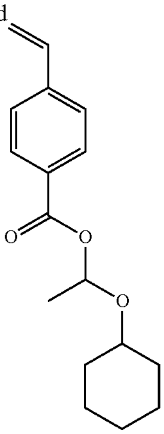
In some aspects, the polymer may have an acid-labile repeating unit that is derived from one or more monomers having a cyclic acetal or cyclic ketal group, for example, having one or more of the following structures:
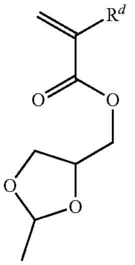
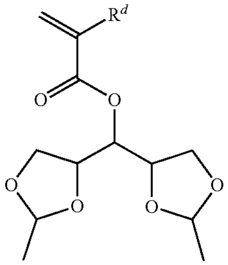
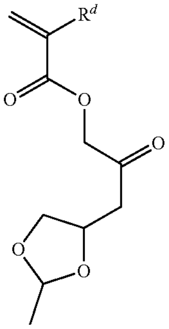
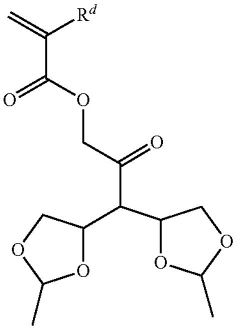
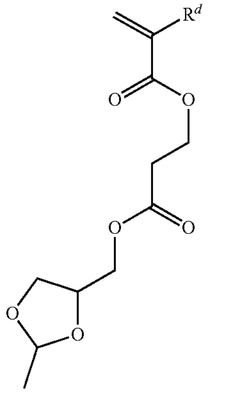
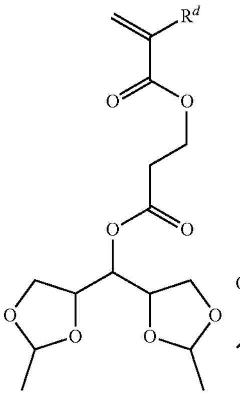
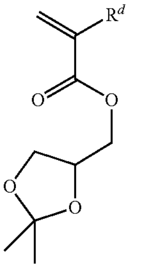
-continued
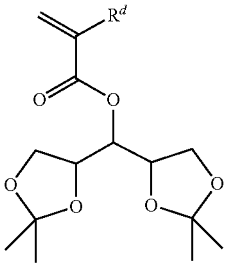
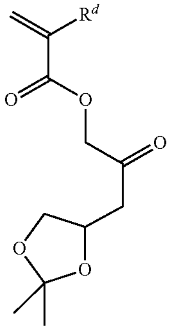
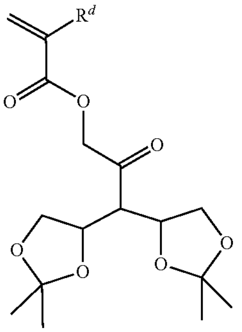
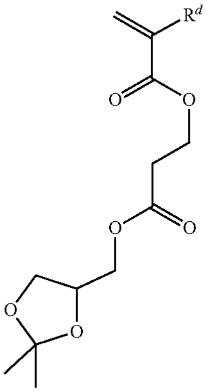
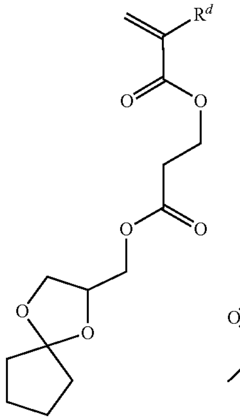
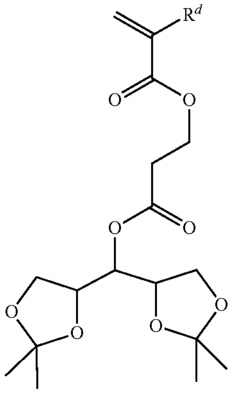
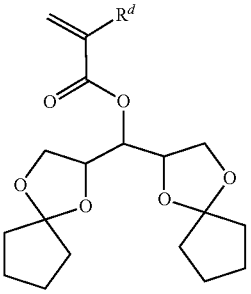
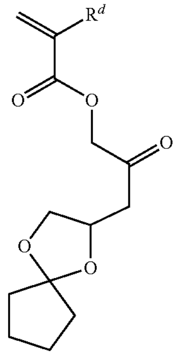

-continued

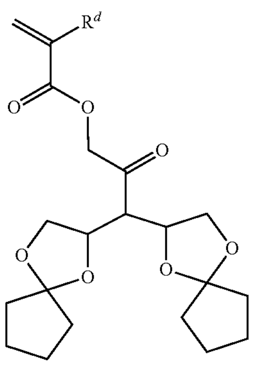

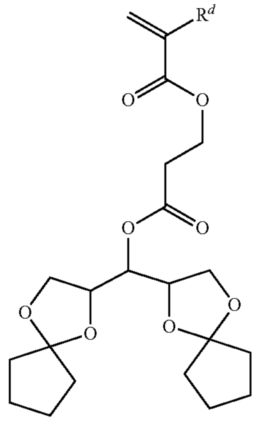

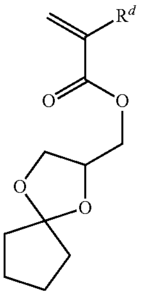

wherein $R^d$ is as defined above for $R^a$.

In some aspects, the polymer may have a repeating unit having an acid-labile group that comprises a tertiary alkoxy group, for example, one or more monomers of the following:

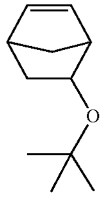

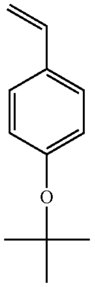

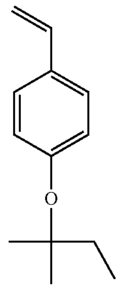

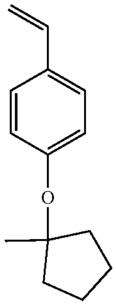

-continued

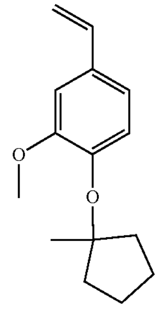

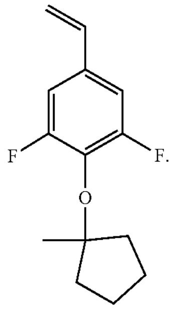

When present, the repeating unit including an acid-labile group is typically included in the polymer in an amount from 5 to 95 mole percent (mol %), more typically from 20 to 80 mol %, still more typically from 30 to 50 mol %, based on total repeating units in the polymer.

In some aspects, the polymer may further include a repeating unit comprising a polar group, where the polar group is pendant to the backbone of the polymer. For example, the polar group can be a lactone group, a hydroxy aryl group, a fluoroalcohol group, or a combination thereof.

In one or more embodiments, the polymer may further include a third repeating unit derived from one or more lactone-containing monomers of Formula (15):

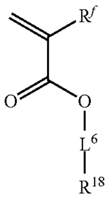

(15)

wherein $R^f$ is hydrogen, fluorine, cyano, or substituted or unsubstituted $C_{1-10}$ alkyl.

In Formula (15), $L^6$ is a single bond or a divalent linking group. Exemplary divalent linking groups for $L^6$ include one or more of substituted or unsubstituted $C_{1-30}$ alkylene, substituted or unsubstituted $C_{1-30}$ heteroalkylene, substituted or unsubstituted $C_{3-30}$ cycloalkylene, substituted or unsubstituted $C_{3-30}$ heterocycloalkylene, substituted or unsubstituted $C_{6-30}$ arylene, substituted or unsubstituted $C_{3-30}$ heteroarylene, —O—, —C(O)—, —C(O)O—, —S—, —$S(O)_2$—, —$N(R^{15a})$—, or —$C(O)N(R^{15b})$—, wherein $R^{15a}$ and $R^{15b}$ may be each independently hydrogen, substituted or unsubstituted $C_{1-20}$ alkyl, substituted or unsubstituted $C_{3-20}$ cycloalkyl, or substituted or unsubstituted $C_{3-20}$ heterocycloalkyl.

In Formula (15), $R^{18}$ is a substituted or unsubstituted $C_{4-20}$ lactone-containing group or a substituted or unsubstituted $C_{4-20}$ sultone-containing group. The $C_{4-20}$ lactone-containing group and the $C_{4-20}$ sultone-containing group may be monocyclic, polycyclic, or fused polycyclic. It is to be understood that when $L^6$ is a single bond, the moiety —$R^{18}$ is directly connected to the oxygen atom adjacent to the carbonyl group (i.e., —C(O)O—$R^{18}$).

Exemplary monomers of Formula (15) may include one or more of the following:

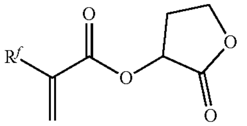

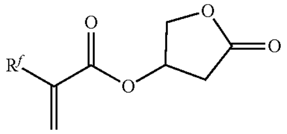

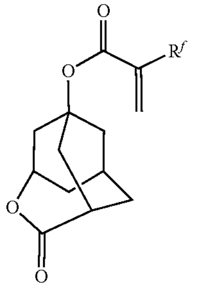

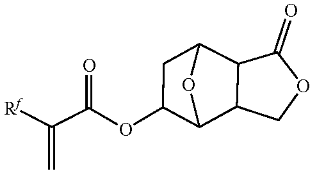

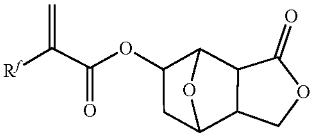

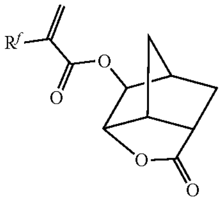

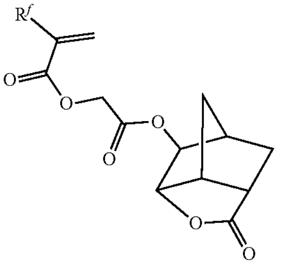

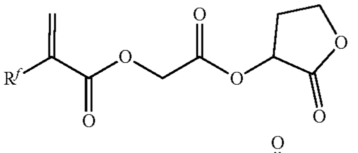

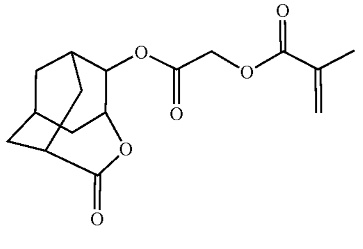

wherein $R^f$ is as defined for Formula (15).

The polymer may include a repeating unit that is base-soluble and/or having a pKa of less than or equal to 12. For example, the repeating unit including a polar group pendant to the backbone of the polymer may be derived from one or more monomers of Formulae (16) to (18):

(16)

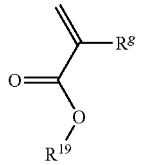

(17)

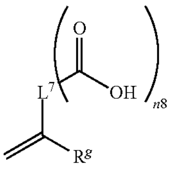

(18)

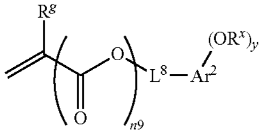

wherein each $R^9$ may be hydrogen, fluorine, cyano, or substituted or unsubstituted $C_{1-10}$ alkyl. Preferably, $R^9$ may be hydrogen, fluorine, or substituted or unsubstituted $C_{1-5}$ alkyl, typically methyl.

In Formula (16), $R^{19}$ may be substituted or unsubstituted $C_{1-60}$ or $C_{1-20}$ alkyl, typically $C_{1-5}$ alkyl; substituted or unsubstituted $C_{3-30}$ or $C_{3-20}$ cycloalkyl; or substituted or unsubstituted poly($C_{1-3}$ alkylene oxide). Preferably, the substituted $C_{L-60}$ or $C_{1-20}$ alkyl, the substituted $C_{3-30}$ or $C_{3-20}$ cycloalkyl, and the substituted poly($C_{1-3}$ alkylene oxide) are substituted with one or more of halogen, a fluoroalkyl group such as a $C_{1-4}$ fluoroalkyl group, typically fluoromethyl, a sulfonamide group —NH—S(O)$_2$—$Y^1$ where $Y^1$ is F or $C_{1-4}$ perfluoroalkyl (e.g., —$NHSO_2CF_3$), or a fluoroalcohol group (e.g., —$C(CF_3)_2OH$).

In Formula (17), $L^7$ may be a single bond or a multivalent linking group chosen, for example, from optionally substituted aliphatic, such as $C_{1-6}$ alkylene or $C_{3-20}$ cycloalkylene, and aromatic hydrocarbons, and combinations thereof, optionally with one or more linking moieties chosen from —O—, —C(O)—, —C(O)O—, —S—, —S(O)$_2$—, —$NR^{17a}$—, or —C(O)N($R^{17b}$)—, wherein $R^{17a}$ and $R^{17b}$ are each chosen from hydrogen and optionally substituted $C_{1-10}$ alkyl. For example, the polymer may further include a repeating unit derived from one or more monomers of Formula (17) wherein $L^7$ is a single bond or a multivalent linking group selected from substituted or unsubstituted $C_{1-20}$ alkylene, typically $C_{1-6}$ alkylene; substituted or unsubstituted $C_{3-20}$ cycloalkylene; typically, $C_{3-10}$ cycloalkylene; and substituted or unsubstituted $C_{6-24}$ arylene.

In Formula (17), n8 is an integer from 1 to 5, typically 1. It is to be understood that when n8 is 1, the group $L^7$ is a divalent linking group. It is to be understood that when n8 is 2, the group $L^7$ is a trivalent linking group. Similarly, it is to be understood that when n8 is 3, the group $L^7$ is a tetravalent linking group; when n8 is 4, the group $L^7$ is a pentavalent linking group; and when n8 is 5, the group $L^7$ is a hexavalent linking group. Accordingly, in the context of Formula (17), the term "multivalent linking group" refers to any of a divalent, trivalent, tetravalent, pentavalent, and/or hexavalent linking groups.

In Formula (18), $L^8$ represents a single bond or a divalent linking group. Preferably, $L^8$ may be a single bond, substituted or unsubstituted $C_{6-30}$ arylene, or substituted or unsubstituted $C_{6-30}$ cycloalkylene.

In Formula (18), n9 is 0 or 1. It is to be understood that when n9 is 0, the moiety represented by —OC(O)— is a single bond such that $L^8$ is directly connected to the alkenyl (vinylic) carbon atom.

In Formula (18), $Ar^1$ is a substituted $C_{5-60}$ aromatic group that optionally includes one or more aromatic ring heteroatoms chosen from N, O, S, or a combination thereof, wherein the aromatic group may be monocyclic, non-fused polycyclic, or fused polycyclic. When the $C_{5-60}$ aromatic group is polycyclic, the ring or ring groups may be fused (such as naphthyl or the like), non-fused, or a combination thereof. When the polycyclic $C_{5-60}$ aromatic group is non-fused, the ring or ring groups may be directly linked (such as biaryls, biphenyl, or the like) or may be bridged by a heteroatom (such as triphenylamino or diphenylene ether). In some aspects, the polycyclic $C_{5-60}$ aromatic group may include a combination of fused rings and directly linked rings (such as binaphthyl or the like).

In Formula (18), y may be an integer from 1 to 12, preferably from 1 to 6, and typically from 1 to 3. Each $R^x$ is independently hydrogen or methyl.

Non-limiting examples of monomers of Formulae (16) to (18) include one or more of the following:

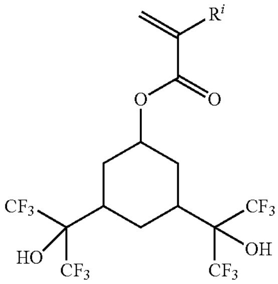
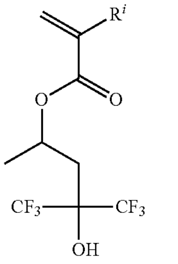
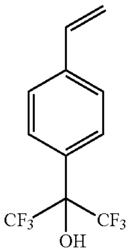
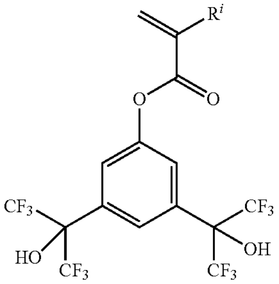
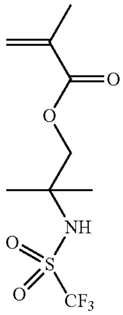
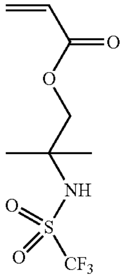
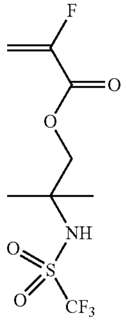
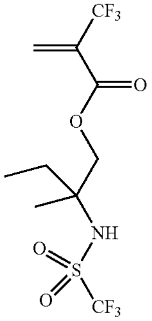

-continued

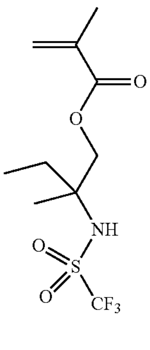
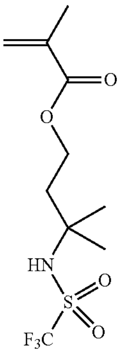
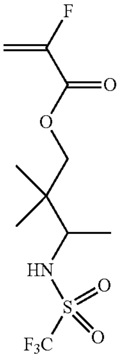
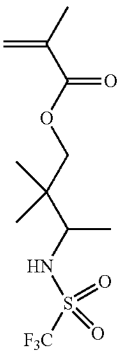
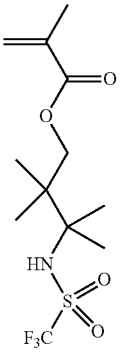
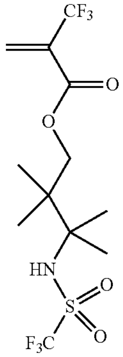
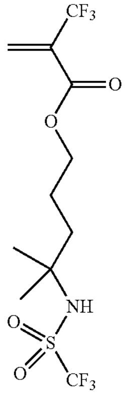
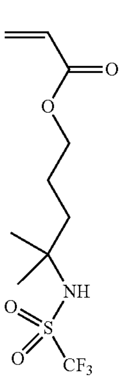
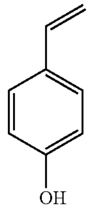
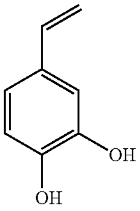
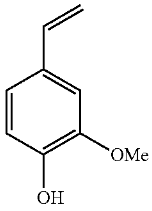
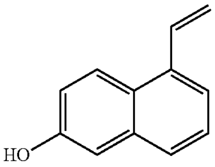
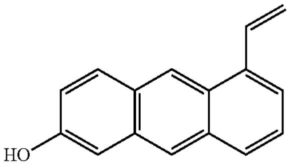
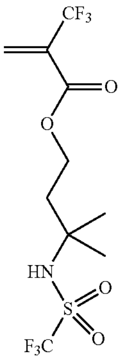
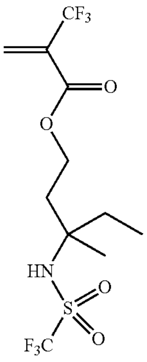
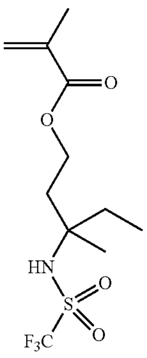

-continued

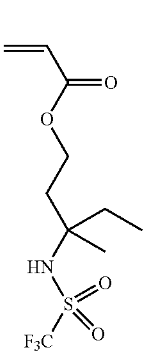
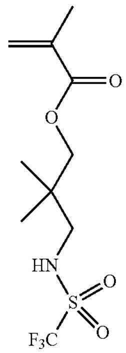
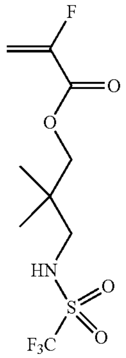
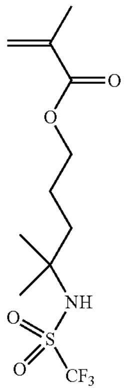
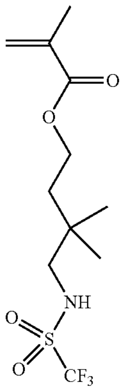
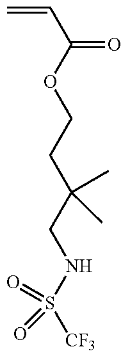
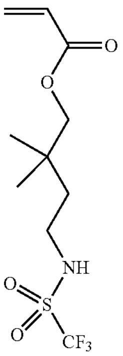
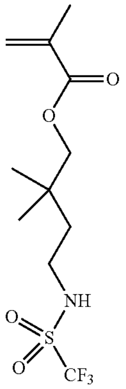
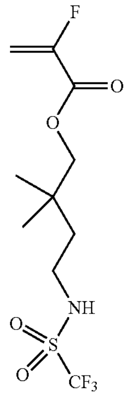
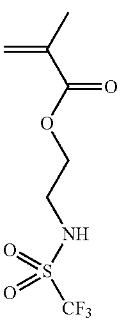
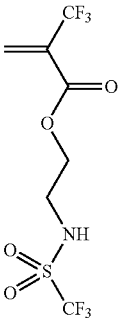
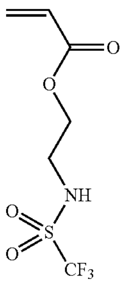
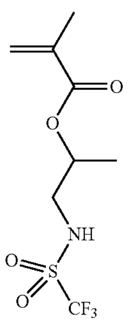

-continued

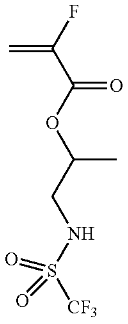
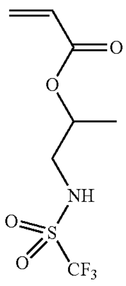
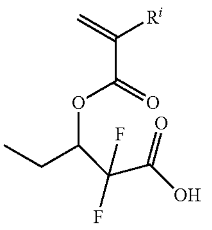
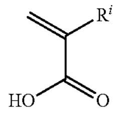
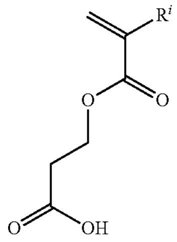
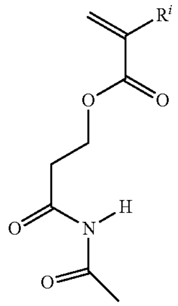

wherein $Y^1$ is as described above, and $R^1$ is as defined for $R^8$ in Formulae (16) to (18).

When present, the polymer typically includes a repeating unit comprising a polar group (e.g., pendant to a backbone of the polymer) in an amount from 1 to 60 mol %, typically from 5 to 50 mol %, more typically from 5 to 40 mol %, based on total repeating units in the polymer.

Non-limiting exemplary polymers of the present invention include one or more of the following:

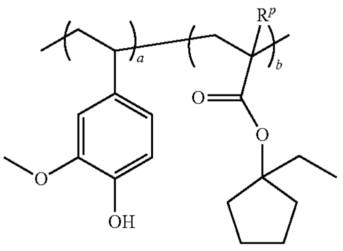

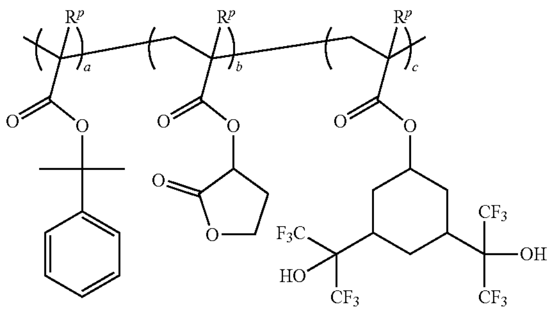

-continued

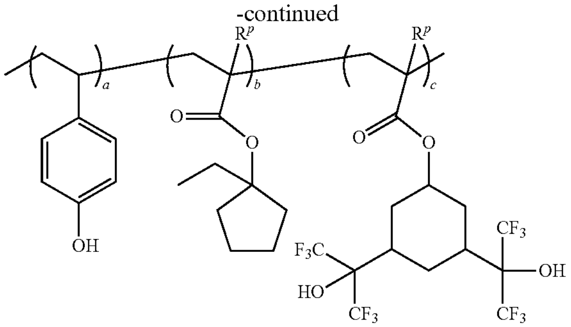

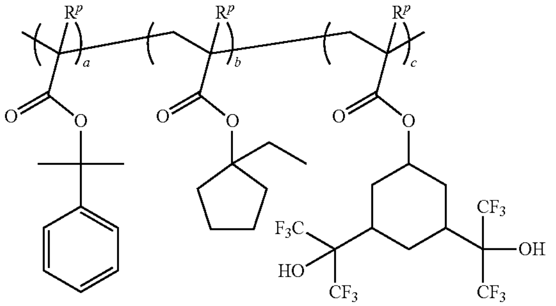

wherein each $R^P$ is as defined for $R^a$ herein, and is typically methyl; and a, b, and c represent the mole fractions for the respective repeating units of the polymer.

The polymer typically has a weight average molecular weight ($M_w$) from 1,000 to 50,000 Dalton (Da), preferably from 2,000 to 30,000 Da, more preferably 4,000 to 25,000 Da, and still more preferably from 5,000 to 25,000 Da. The polydispersity index (PDI) of the first polymer, which is the ratio of $M_W$ to number average molecular weight ($M_n$) is typically from 1.1 to 3, and more typically from 1.1 to 2. Molecular weight values are determined by gel permeation chromatography (GPC) using polystyrene standards.

The polymer, if used, typically may be present in the photoresist composition in an amount from 10 to 99.9 wt %, typically from 25 to 99 wt %, and more typically from 40 to 95 wt % or from 60 to 95 wt %, based on total solids of the photoresist composition. In some aspects, the photoresist composition may include from 0.5 to 6 wt % of the inventive compound and from 40 to 95 wt % of a polymer, or the photoresist composition may include from 1 to 5 wt % of the inventive compound and from 60 to 85 wt % of a polymer.

The polymer may be prepared using any suitable method(s) in the art. For example, one or more monomers corresponding to the repeating units described herein may be combined, or fed separately, using suitable solvent(s) and initiator, and polymerized in a reactor. For example, the polymer may be obtained by polymerization of the respective monomers under any suitable conditions, such as by heating at an effective temperature, irradiation with activating radiation at an effective wavelength, or a combination thereof.

Suitable PAGs can generate an acid that, during post-exposure bake (PEB), causes cleavage of acid-labile groups present on a polymer of the photoresist composition. The PAG may be in non-polymeric form or in polymeric form, for example, present in a polymerized repeating unit of the polymer as described above, or as part of a different polymer. In some embodiments, the PAG may be included in the composition as a non-polymerized PAG compound, as a repeating unit of a polymer having a PAG moiety that is derived from a polymerizable PAG monomer, or as a combination thereof.

Suitable non-polymeric PAG compounds may have Formula $G^+A^-$, wherein $G^+$ is an organic cation chosen from iodonium cations substituted with two alkyl groups, two aryl groups, or a combination of alkyl and aryl groups; and sulfonium cations substituted with three alkyl groups, three aryl groups, or a combination of alkyl and aryl groups, and $A^-$ is a non-polymerizable organic anion.

Particularly suitable non-polymeric organic anions include those, the conjugated acids of which have a pKa of from −15 to 1. Particularly preferred anions are fluorinated alkyl sulfonates and fluorinated sulfonimides.

Useful non-polymeric PAG compounds are known in the art of chemically amplified photoresists and include, for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; di-t-butyphenyliodonium perfluorobutanesulfonate, and di-t-butyphenyliodonium camphorsulfonate. Non-ionic sulfonates and sulfonyl compounds are also known to function as photoacid generators, e.g., nitrobenzyl derivatives, for example, 2-nitrobenzyl-p-toluenesulfonate, 2,6-dinitrobenzyl-p-toluenesulfonate, and 2,4-dinitrobenzyl-p-toluenesulfonate; sulfonic acid esters, for example, 1,2,3-tris(methanesulfonyloxy)benzene, 1,2,3-tris(trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O—(p-toluenesulfonyl)-α-dimethylglyoxime, and bis-O—(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1,3,5-triazine, and 2-(4-methoxynaphthyl)-4,6-bis(trichloromethyl)-1,3,5-triazine. Suitable non-polymerized photoacid generators are further described in U.S. Pat. No. 8,431,325 to Hashimoto et al. in column 37, lines 11-47 and columns 41-91. Other suitable sulfonate PAGs include sulfonated esters and sulfonyloxy ketones, nitrobenzyl esters, s-triazine derivatives, benzoin tosylate, t-butylphenyl α-(p-toluenesulfonyloxy)acetate, and t-butyl α-(p-toluenesulfonyloxy)acetate; as described in U.S. Pat. Nos. 4,189,323 and 8,431,325.

Typically, when the photoresist composition includes a non-polymeric photoacid generator, it is present in the photoresist composition in an amount of from 0.3 to 65 weight percent (wt %), more typically 1 to 20 wt %, based on total solids of the photoresist composition.

In some embodiments, $G^+$ may be a sulfonium cation of Formula (19) or an iodonium cation of Formula (20):

(19)

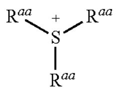

(20)

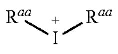

In Formulae (19) and (20), each $R^{aa}$ is independently substituted or unsubstituted $C_{1-20}$ alkyl, substituted or unsubstituted $C_{3-20}$ cycloalkyl, substituted or unsubstituted $C_{2-20}$ alkenyl, substituted or unsubstituted $C_{6-30}$ aryl, substituted or unsubstituted $C_{3-30}$ heteroaryl, substituted or unsubstituted $C_{7-20}$ arylalkyl, or substituted or unsubstituted $C_{4-20}$ heteroarylalkyl. Each $R^{aa}$ may be either separate or connected to another group $R^{aa}$ via a single bond or a divalent linking group to form a ring. Each $R^{aa}$ optionally may include as part of its structure a divalent linking group. Each $R^{aa}$ independently may optionally comprise an acid-labile group chosen, for example, from tertiary alkyl ester groups, secondary or tertiary aryl ester groups, secondary or tertiary ester groups having a combination of alkyl and aryl groups, tertiary alkoxy groups, acetal groups, or ketal groups.

Exemplary sulfonium cations of Formula (19) include one or more of the following:

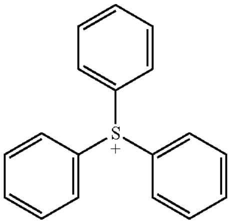

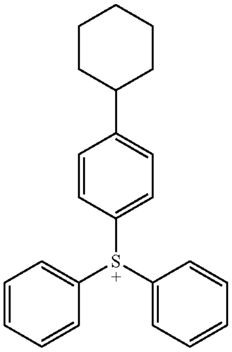

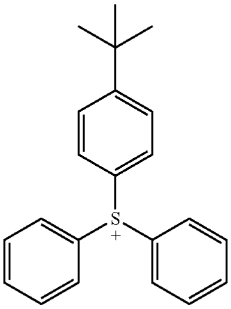

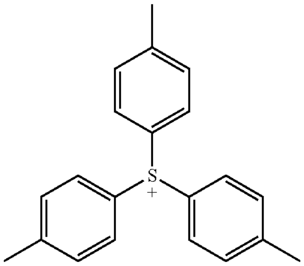

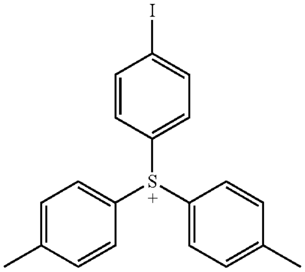

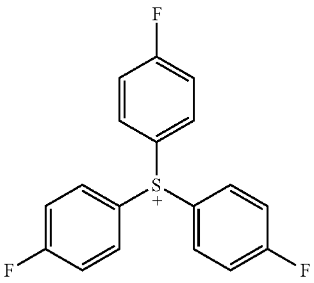

-continued

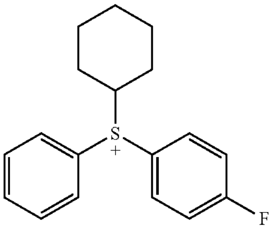

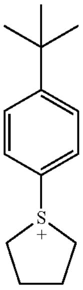

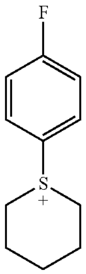

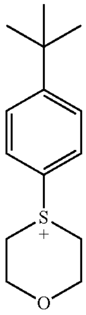

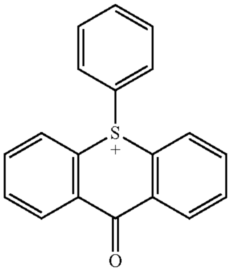

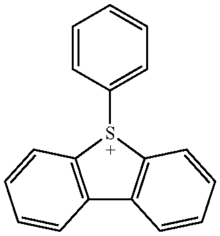

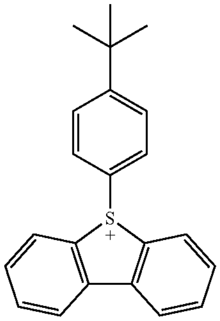

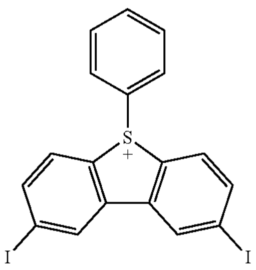

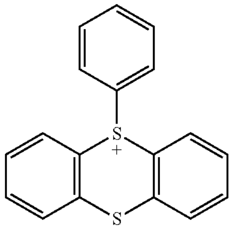

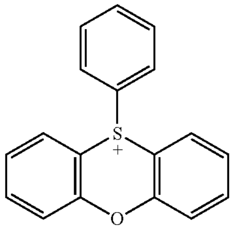

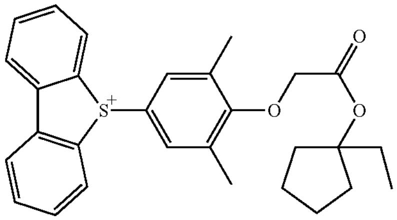

-continued
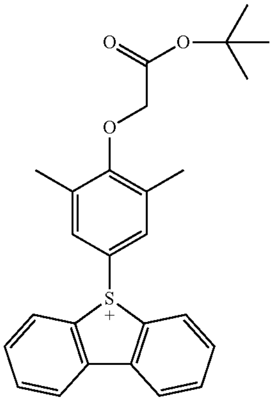
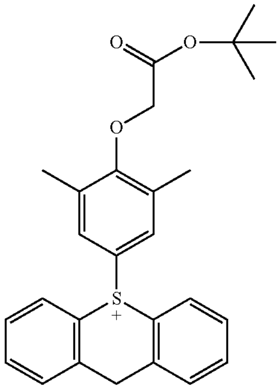
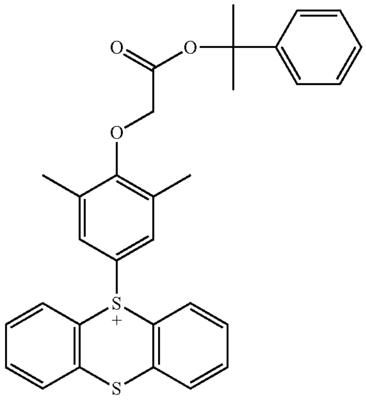
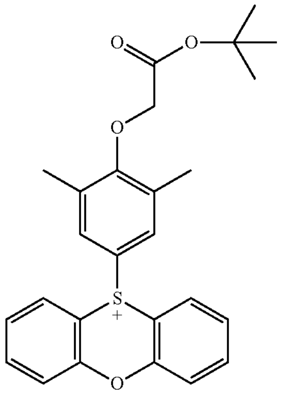
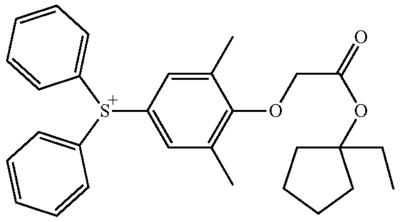
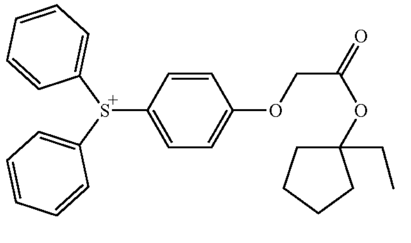
-continued
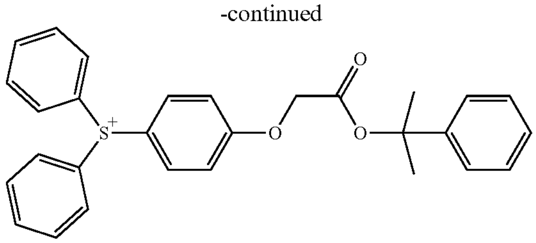
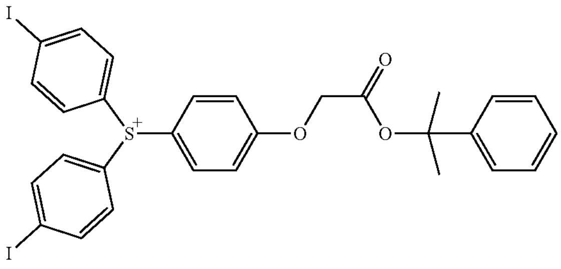
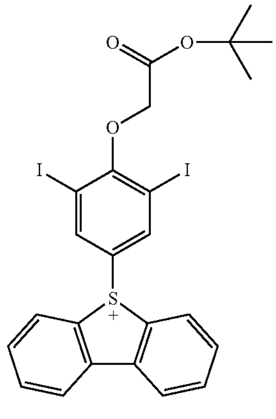
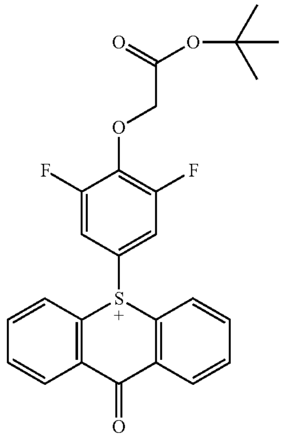
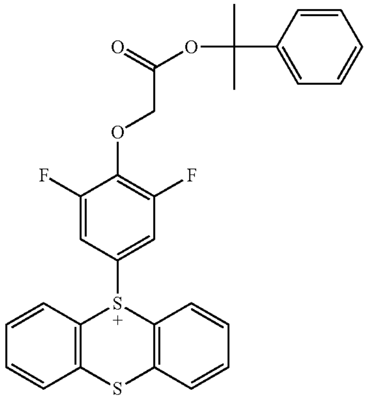
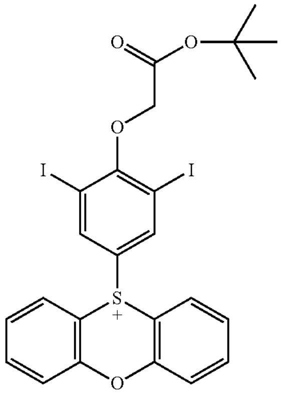

-continued
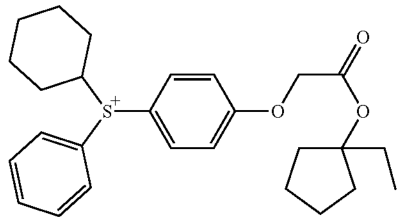
Exemplary iodonium cations of Formula (20) include one or more of the following:
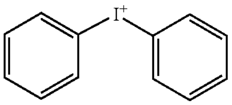
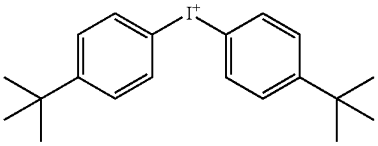
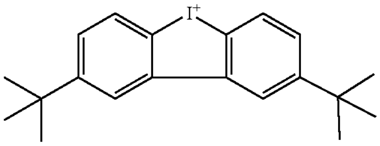
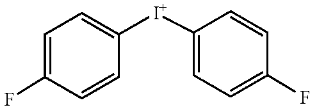
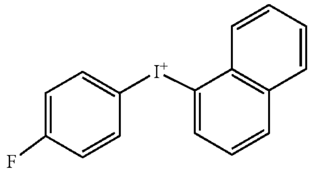
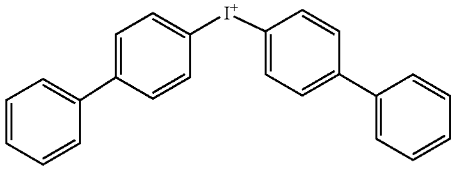
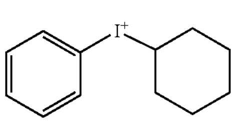
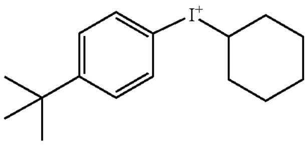
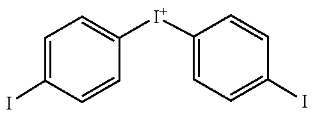
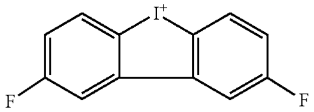
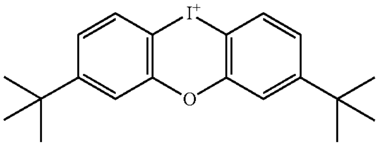
-continued
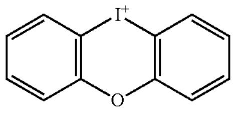
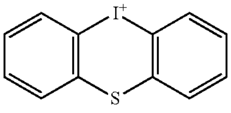
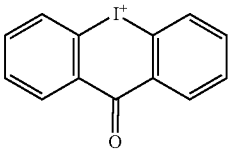
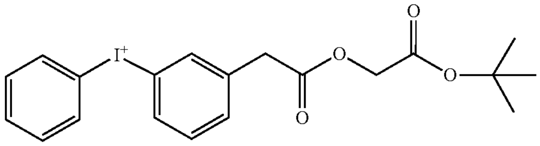
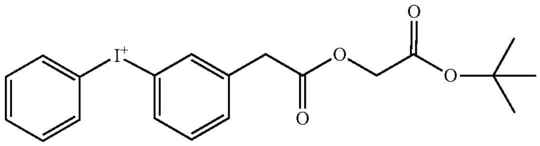
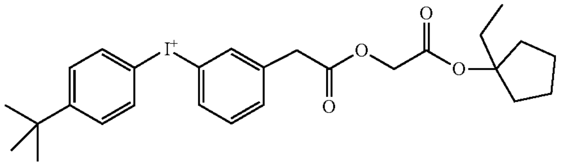
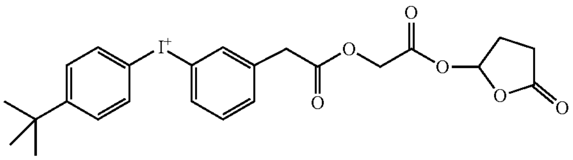
PAGs that are onium salts typically comprise an organic anion having a sulfonate group or a non-sulfonate-type group, such as sulfonamidate, sulfonimidate, methide, or borate.
Exemplary organic anions having a sulfonate group include one or more of the following:
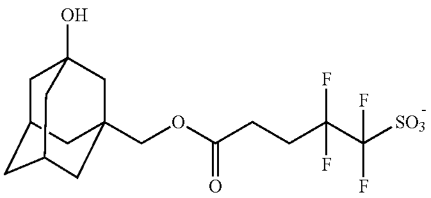
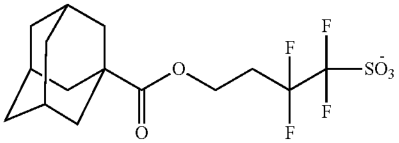
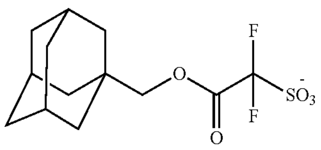

-continued
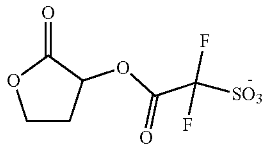
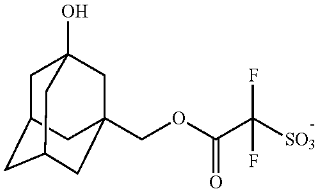
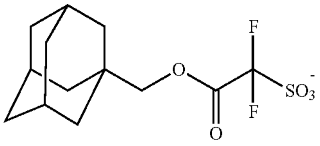
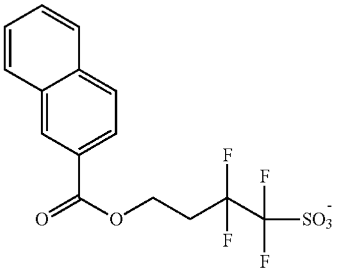
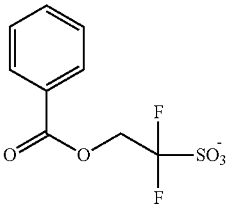
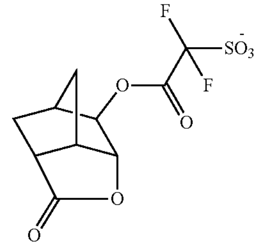
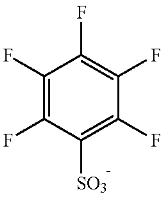
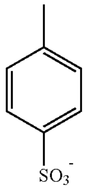
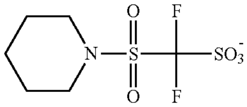
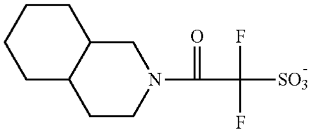
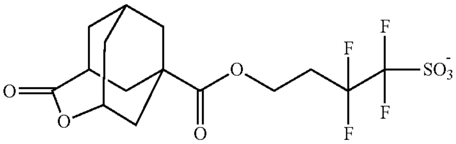
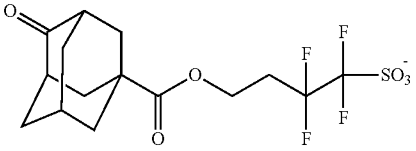
-continued
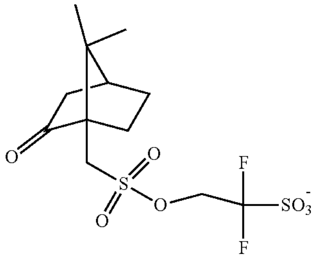
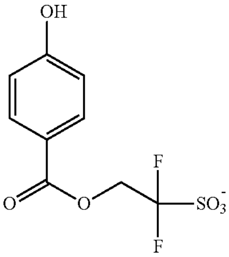
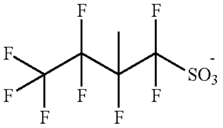
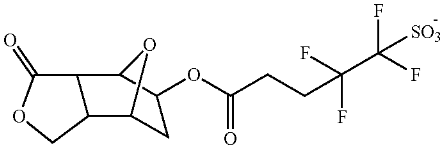
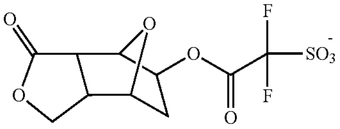
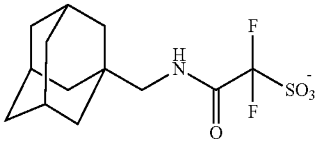
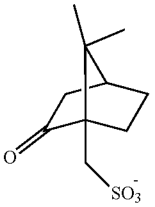
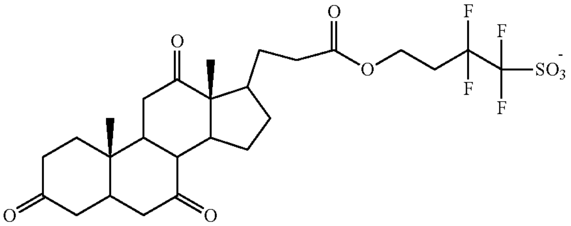
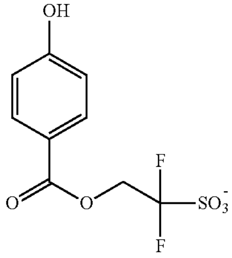
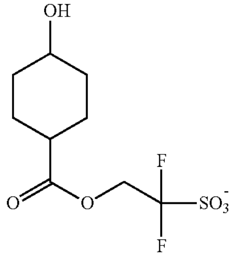
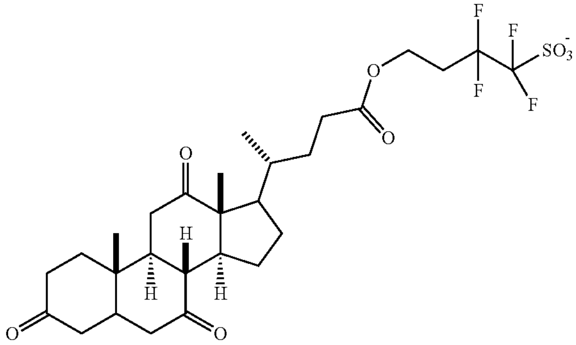

-continued

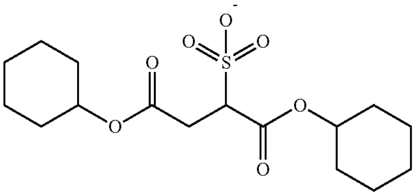

Exemplary non-sulfonated anions include one or more of the following:

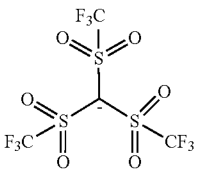
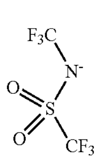
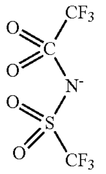
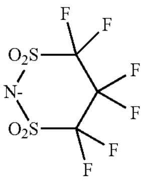
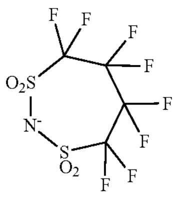
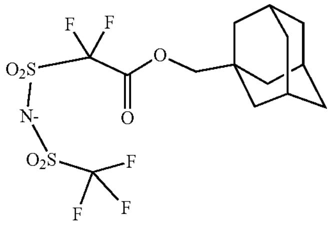
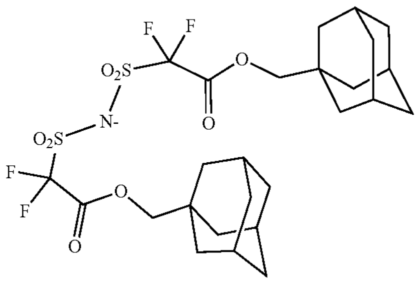
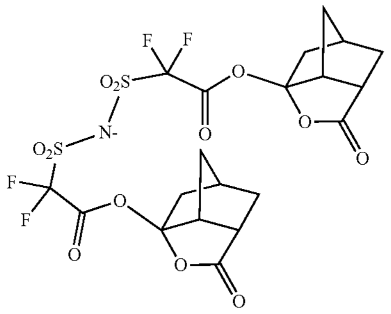
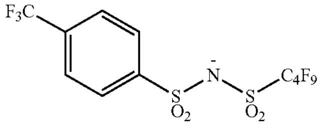
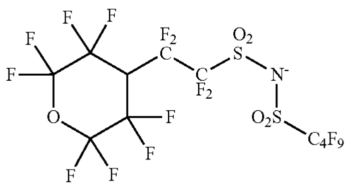
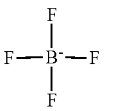

-continued

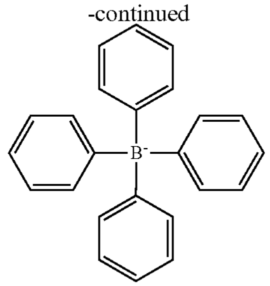

The photoresist composition may optionally comprise a plurality of PAGs. The plurality of PAGs may be polymeric, non-polymeric, or may include both polymeric and non-polymeric PAGs. Preferably, each PAG of the plurality of PAGs is non-polymeric.

In one or more aspects, the photoresist composition may include a first photoacid generator that includes a sulfonate group on the anion, and the photoresist composition may include a second photoacid generator that is non-polymeric, wherein the second photoacid generator may include an anion that is free of sulfonate groups.

In some aspects, the polymer optionally may further include a repeating unit that comprises a PAG-containing moiety, for example a repeating unit derived from one or more monomers of Formula (21):

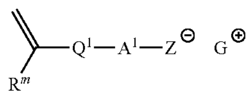
(21)

wherein R‴ may be hydrogen, fluorine, cyano, or substituted or unsubstituted $C_{1-10}$ alkyl. Preferably, R‴ is hydrogen, fluorine, or substituted or unsubstituted $C_{1-5}$ alkyl, typically methyl.

In Formula (21), $Q^1$ may be a single bond or a divalent linking group. Preferably, $Q^1$ may include 1 to 10 carbon atoms and at least one heteroatom, more preferably —C(O)—O—. $A^1$ may be one or more of substituted or unsubstituted $C_{1-30}$ alkylene, substituted or unsubstituted $C_{3-30}$ cycloalkylene, substituted or unsubstituted $C_{3-30}$ heterocycloalkylene, substituted or unsubstituted $C_{6-30}$ arylene, or substituted or unsubstituted $C_{3-30}$ heteroarylene. Preferably, $A^1$ may be a divalent $C_{1-30}$ perfluoroalkylene group that is optionally substituted. Z— is an anionic moiety with a negative charge (i.e., Z has a negative charge), the conjugated acid of which typically has a pKa from −15 to 1. For example, Z— may be a sulfonate anion, a carboxylate anion, an anion of a sulfonamide, an anion of a sulfonimide, or a methide anion. Particularly preferred anion moieties are fluorinated alkyl sulfonates and fluorinated sulfonimides. $G^+$ is an organic cation having a positive charge (i.e., G has a positive charge). In some embodiments, $G^+$ is an iodonium cation substituted with two alkyl groups, two aryl groups, or a combination of alkyl and aryl groups; or a sulfonium cation substituted with three alkyl groups, three aryl groups, or a combination of alkyl and aryl groups.

Exemplary monomers of Formula (21) include one or more of the following:

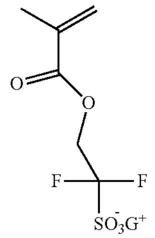
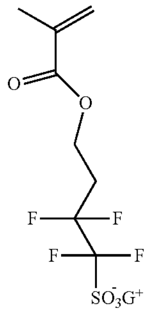
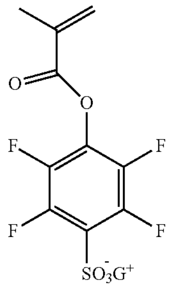
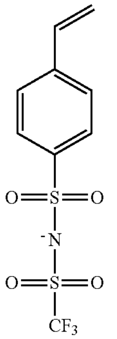
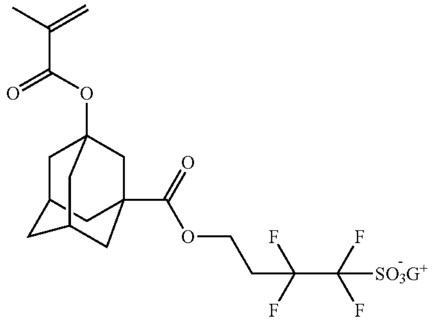
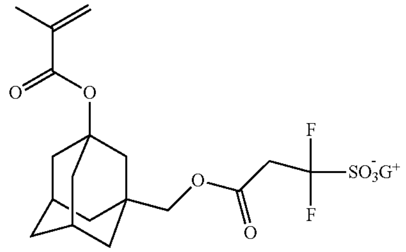
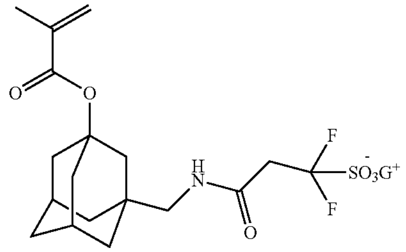
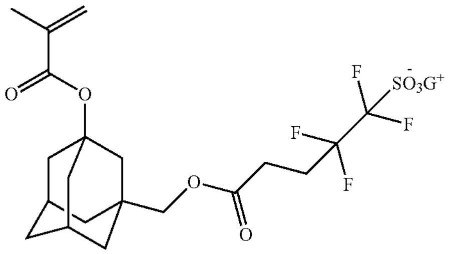
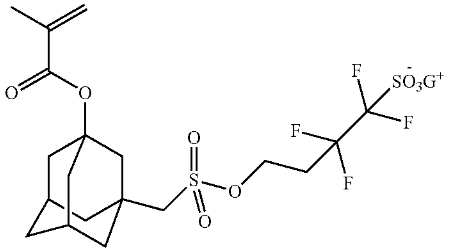

-continued

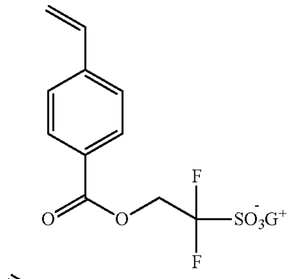
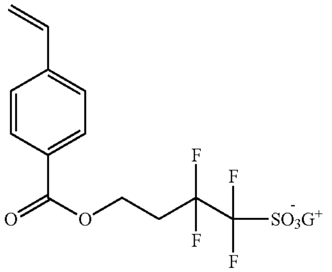

wherein $G^+$ is an organic cation as defined herein.

When used, the repeating unit comprising a PAG moiety can be included in a polymer in an amount from 1 to 15 mol %, typically from 1 to 8 mol %, more typically from 2 to 6 mol %, based on total repeating units in the polymer.

The photoresist composition further includes a solvent for dissolving the components of the composition and to facilitate its coating on a substrate. Preferably, the solvent is an organic solvent conventionally used in the manufacture of electronic devices. Suitable solvents include, for example: aliphatic hydrocarbons such as hexane and heptane; aromatic hydrocarbons such as toluene and xylene; halogenated hydrocarbons such as dichloromethane, 1,2-dichloroethane and 1-chlorohexane; alcohols such as methanol, ethanol, 1-propanol, iso-propanol, tert-butanol, 2-methyl-2-butanol, 4-methyl-2-pentanol, and diacetone alcohol (4-hydroxy-4-methyl-2-pentanone); propylene glycol monomethyl ether (PGME); ethers such as diethyl ether, tetrahydrofuran, 1,4-dioxane, and anisole; ketones such as acetone, methyl ethyl ketone, methyl iso-butyl ketone, 2-heptanone, and cyclohexanone (CHO); esters such as ethyl acetate, n-butyl acetate, propylene glycol monomethyl ether acetate (PGMEA), ethyl lactate (EL), hydroxyisobutyrate methyl ester (HBM), and ethyl acetoacetate; lactones such as gamma-butyrolactone (GBL) and epsilon-caprolactone; lactams such as N-methyl pyrrolidone; nitriles such as acetonitrile and propionitrile; cyclic or non-cyclic carbonate esters such as propylene carbonate, dimethyl carbonate, ethylene carbonate, propylene carbonate, diphenyl carbonate, and propylene carbonate; polar aprotic solvents such as dimethyl sulfoxide and dimethyl formamide; water; and combinations thereof. Of these, preferred solvents are PGME, PGMEA, EL, GBL, HBM, CHO, and combinations thereof.

The total solvent content (i.e., cumulative solvent content for all solvents) in the photoresist compositions is typically from 40 to 99 wt %, for example, from 50 to 99 wt %, or from 85 to 99 wt %, based on total solids of the photoresist composition. The desired solvent content will depend, for example, on the desired thickness of the coated photoresist layer and coating conditions.

In some aspects, the photoresist composition may further include a material that comprises one or more base-labile groups (a "base-labile material"). As referred to herein, base-labile groups are functional groups that can undergo cleavage reaction to provide polar groups such as hydroxyl, carboxylic acid, sulfonic acid, and the like, in the presence of an aqueous alkaline developer after exposure and post-exposure baking steps. The base-labile group will not react significantly (e.g., will not undergo a bond-breaking reaction) prior to a development step of the photoresist composition that comprises the base-labile group. Thus, for instance, a base-labile group will be substantially inert during pre-exposure soft-bake, exposure, and post-exposure bake steps. By “substantially inert” it is meant that:5%, typically 1%, of the base-labile groups (or moieties) will decompose, cleave, or react during the pre-exposure soft-bake, exposure, and post-exposure bake steps. The base-labile group is reactive under typical photoresist development conditions using, for example, an aqueous alkaline photoresist developer such as a 0.26 normal (N) aqueous solution of tetramethylammonium hydroxide (TMAH). For example, a 0.26 N aqueous solution of TMAH may be used for single puddle development or dynamic development, e.g., where the 0.26 N TMAH developer is dispensed onto an imaged photoresist layer for a suitable time such as 10 to 120 seconds (s). An exemplary base-labile group is an ester group, typically a fluorinated ester group. Preferably, the base-labile material is substantially not miscible with and has a lower surface energy than the polymer and other solid components of the photoresist composition. When coated on a substrate, the base-labile material can thereby segregate from other solid components of the photoresist composition to a top surface of the formed photoresist layer.

In some aspects, the base-labile material may be a polymeric material, also referred to herein as a base-labile polymer, which may include one or more repeating units comprising one or more base-labile groups. For example, the base-labile polymer may comprise a repeating unit comprising 2 or more base-labile groups that are the same or different. A preferred base-labile polymer includes at least one repeating unit comprising 2 or more base-labile groups, for example a repeating unit comprising 2 or 3 base-labile groups.

The base-labile polymer may be a polymer comprising a repeating unit derived from one or more monomers of Formula (16):

(22)

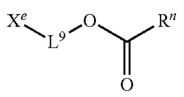

wherein $X^e$ is a polymerizable group selected from $C_2$ alkenyl and (meth)acrylic, $L^9$ is a divalent linking group; and $R^{15}$ is substituted or unsubstituted $C_{1-20}$ fluoroalkyl, provided that the carbon atom bonded to the carbonyl (—C(O)—) in Formula (22) is substituted with at least one fluorine atom. Exemplary monomers of Formula (22) may include one or more of the following:

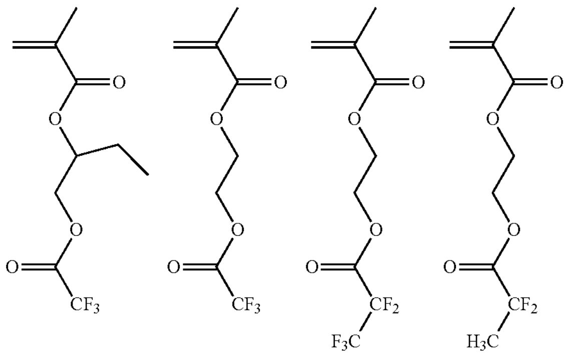

The base-labile polymer may include a repeating unit including two or more base-labile groups. For example, the base-labile polymer can include a repeating unit derived from one or more monomers of Formula (23):

(23)

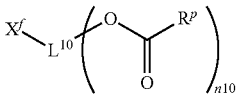

wherein $X^f$ and $R^p$ are as defined in Formula (23) for $X^e$ and $R^n$, respectively; $L^{10}$ is a polyvalent linking group including one or more of substituted or unsubstituted $C_{1-20}$ alkylene, substituted or unsubstituted $C_{3-20}$ cycloalkylene, —C(O)—, or —C(O)O—; and n10 may be an integer of 2 or greater, for example 2 or 3.

Exemplary monomers of Formula (23) include one or more of the following:

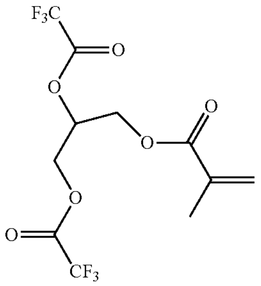

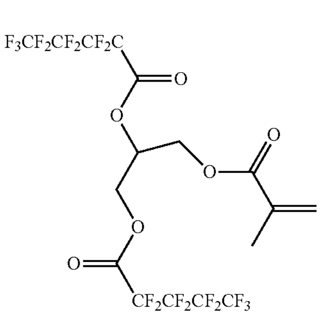

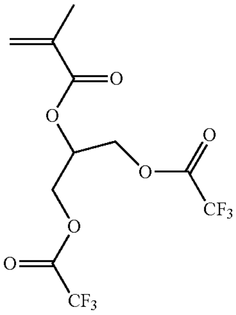

-continued

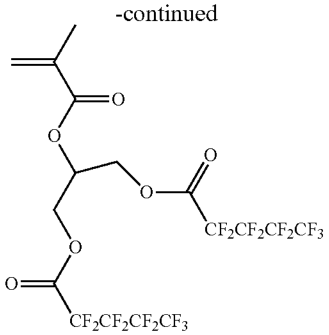

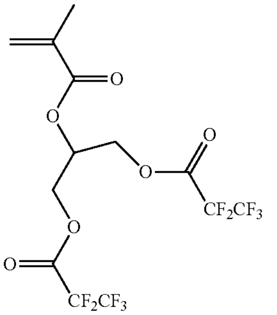

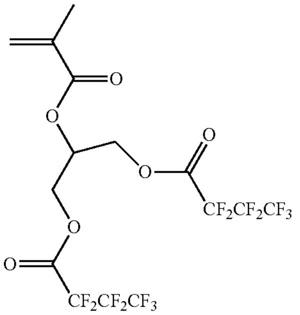

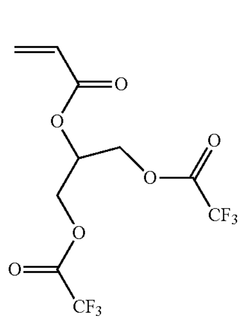

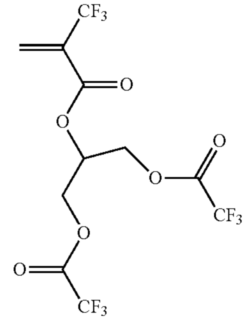

The base-labile polymer may include a repeating unit including one or more base-labile groups. For example, the base-labile polymer can include a repeating unit derived from one or more monomers of Formula (24):

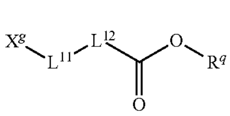

(24)

wherein $X^g$ and $R^q$ are as defined in Formula (24) for $X^e$ and $R''$, respectively; $L^{11}$ is a divalent linking group; and $L^{12}$ is substituted or unsubstituted $C_{1-20}$ fluoroalkylene wherein the carbon atom bonded to the carbonyl (—C(O)—) in Formula (24) is substituted with at least one fluorine atom. Exemplary monomers of Formula (24) include one or more of the following:

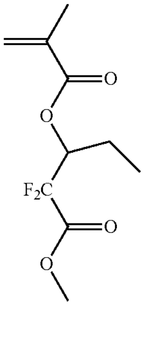

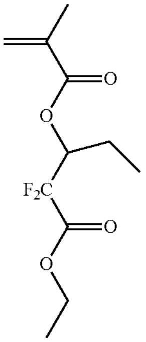

In some aspects, a base-labile polymer may comprise one or more base-labile groups and one or more acid-labile groups, such as one or more acid-labile ester moieties (e.g., t-butyl ester) or acid-labile acetal groups. For example, the base-labile polymer may comprise a repeating unit including a base-labile group and an acid-labile group, i.e., wherein both a base-labile group and an acid-labile group are present on the same repeating unit. In another example, the base-labile polymer may comprise a first repeating unit comprising a base-labile group and a second repeating unit comprising an acid-labile group.

The base-labile polymer may be prepared using any suitable methods in the art. For example, the base-labile polymer may be obtained by polymerization of the respective monomers under any suitable conditions, such as by heating at an effective temperature, irradiation with activating radiation at an effective wavelength, or a combination thereof. Additionally, or alternatively, one or more base-labile groups may be grafted onto the backbone of a polymer using suitable methods.

In some aspects, the base-labile material is a single molecule comprising one more base-labile ester groups, preferably one or more fluorinated ester groups. The base-labile materials that are single molecules typically have a $M_w$ in the range from 50 to 1,500 Da. Exemplary base-labile materials include one or more of the following:

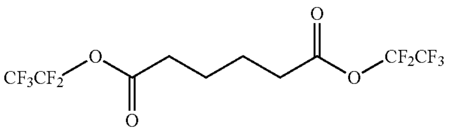

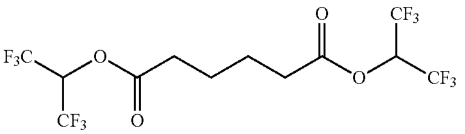

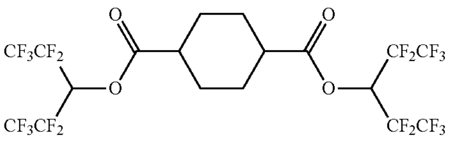

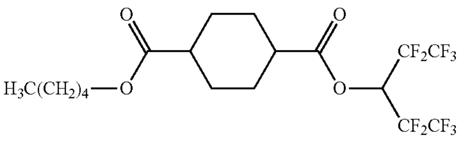

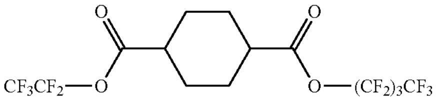

-continued

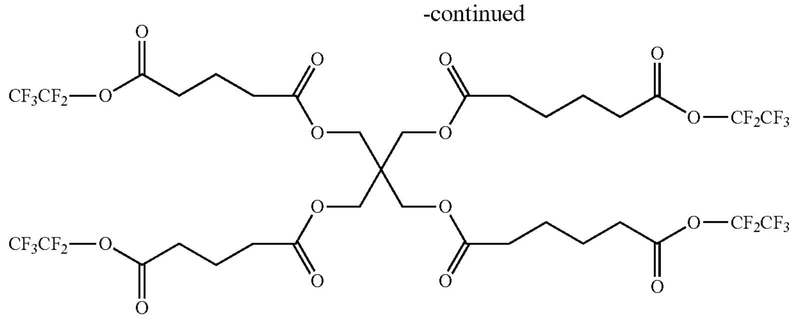

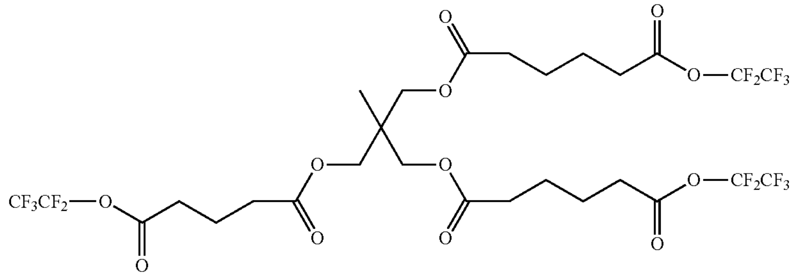

When present, the base-labile material is typically present in the photoresist compositions in an amount of from 0.01 to 10 wt %, typically 1 to 5 wt %, based on total solids of the photoresist composition.

Additionally, or alternatively, to the base-labile polymer, the photoresist compositions may further include one or more polymers in addition to and different from the photoresist polymer described above. For example, the photoresist compositions may include an additional polymer as described above but different in composition, or a polymer that is similar to those described above but does not include each of the requisite repeating units. Additionally, or alternatively, the one or more additional polymers may include those well known in the photoresist art, for example, those chosen from polyacrylates, polyvinylethers, polyesters, polynorbornenes, polyacetals, polyethylene glycols, polyamides, polyacrylamides, polyphenols, novolacs, styrenic polymers, polyvinyl alcohols, or combinations thereof.

The photoresist composition may further include one or more additional, optional additives. For example, optional additives may include actinic and contrast dyes, anti-striation agents, plasticizers, speed enhancers, sensitizers, photo-decomposable quenchers (PDQ) (and, also known as photo-decomposable bases), basic quenchers, thermal acid generators, surfactants, and the like, or combinations thereof. If present, the optional additives are typically present in the photoresist compositions in an amount of from 0.01 to 10 wt %, based on total solids of the photoresist composition.

PDQs generate a weak acid upon irradiation. The acid generated from a photo-decomposable quencher is not strong enough to react rapidly with acid-labile groups that are present in the resist matrix. Exemplary photo-decomposable quenchers include, for example, photo-decomposable cations, and preferably those also useful for preparing strong acid generator compounds, paired with an anion of a weak acid (pKa>1) such as, for example, an anion of a $C_{1-20}$ carboxylic acid or $C_{1-20}$ sulfonic acid.

Exemplary carboxylic acids include formic acid, acetic acid, propionic acid, tartaric acid, succinic acid, cyclohexanecarboxylic acid, benzoic acid, salicylic acid, and the like. Exemplary sulfonic acids include p-toluene sulfonic acid, camphor sulfonic acid and the like. In a preferred embodiment, the photo-decomposable quencher is a photo-decomposable organic zwitterion compound such as diphenyliodonium-2-carboxylate.

The photo-decomposable quencher may be in non-polymeric or polymer-bound form. When in polymeric form, the photo-decomposable quencher is present in polymerized units on the first polymer or second polymer. The polymerized units containing the photo-decomposable quencher are typically present in an amount from 0.1 to 30 mol %, preferably from 1 to 10 mol % and more preferably from 1 to 2 mol %, based on total repeating units of the polymer.

Exemplary basic quenchers include, for example, linear aliphatic amines such as tributylamine, trioctylamine, triisopropanolamine, tetrakis(2-hydroxypropyl)ethylenediamine: n-tert-butyldiethanolamine, tris(2-acetoxy-ethyl) amine, 2,2', 2", 2'"-(ethane-1,2-diylbis(azanetriyl))tetraethanol, 2-(dibutylamino)ethanol, and 2,2',2"-nitrilotriethanol; cyclic aliphatic amines such as 1-(tert-butoxycarbonyl)-4-hydroxypiperidine, tert-butyl 1-pyrrolidinecarboxylate, tert-butyl 2-ethyl-1H-imidazole-1-carboxylate, di-tert-butyl piperazine-1,4-dicarboxylate, and N-(2-acetoxy-ethyl) morpholine; aromatic amines such as pyridine, di-tert-butyl pyridine, and pyridinium; linear and cyclic amides and derivatives thereof such as N,N-bis(2-hydroxyethyl)pivalamide, N,N-diethylacetamide, $N^1$,$N^1$,$N^3$, $N^3$-tetrabutylmalonamide, 1-methylazepan-2-one, 1-allylazepan-2-one, and tert-butyl 1,3-dihydroxy-2-(hydroxymethyl)propan-2-ylcarbamate; ammonium salts such as quaternary ammonium salts of sulfonates, sulfamates, carboxylates, and phosphonates; imines such as primary and secondary aldimines and ketimines; diazines such as optionally substituted pyrazine, piperazine, and phenazine; diazoles such as optionally substituted pyrazole, thiadiazole, and imidazole; and optionally substituted pyrrolidones such as 2-pyrrolidone and cyclohexyl pyrrolidine.

The basic quenchers may be in non-polymeric or polymer-bound form. When in polymeric form, the quencher may be present in repeating units of the polymer. The repeating units containing the quencher are typically present in an amount of from 0.1 to 30 mol %, preferably from 1 to 10 mol % and more preferably from 1 to 2 mol %, based on total repeating units of the polymer.

The photoresist composition may further include one or more surfactants, including fluorinated and/or non-fluorinated surfactant(s). The surfactant(s) can be ionic or non-ionic, with non-ionic surfactant(s) being preferable. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova. In an aspect, the photoresist composition further includes a surfactant polymer including a fluorine-containing repeating unit.

Patterning methods using the photoresist compositions of the invention will now be described. Suitable substrates on which the photoresist compositions can be coated include electronic device substrates. A wide variety of electronic device substrates may be used in the present invention, such as: semiconductor wafers; polycrystalline silicon substrates; packaging substrates such as multichip modules; flat panel display substrates; substrates for light emitting diodes (LEDs) including organic light emitting diodes (OLEDs); and the like, with semiconductor wafers being typical. Such substrates are typically composed of one or more of silicon, polysilicon, silicon oxide, silicon nitride, silicon oxynitride, silicon germanium, gallium arsenide, aluminum, sapphire, tungsten, titanium, titanium-tungsten, nickel, copper, and gold. Suitable substrates may be in the form of wafers such as those used in the manufacture of integrated circuits, optical sensors, flat panel displays, integrated optical circuits, and LEDs. Such substrates may be any suitable size. Typical wafer substrate diameters are from 200 to 300 millimeters (mm), although wafers having smaller and larger diameters may be suitably employed according to the present invention. The substrates may include one or more layers or structures which may optionally include active or operable portions of devices being formed.

Typically, one or more lithographic layers such as a hardmask layer, for example, a spin-on-carbon (SOC), amorphous carbon, or metal hardmask layer, a CVD layer such as a silicon nitride (SiN), a silicon oxide (SiO), or silicon oxynitride (SiON) layer, an organic or inorganic underlayer, or combinations thereof, are provided on an upper surface of the substrate prior to coating a photoresist composition of the present invention. Such layers, together with an overcoated photoresist layer, form a lithographic material stack.

Optionally, a layer of an adhesion promoter may be applied to the substrate surface prior to coating the photoresist compositions. If an adhesion promoter is desired, any suitable adhesion promoter for polymer films may be used, such as silanes, typically organosilanes such as trimethoxyvinylsilane, triethoxyvinylsilane, hexamethyldisilazane, or an aminosilane coupler such as gamma-aminopropyltriethoxysilane. Particularly suitable adhesion promoters include those sold under the AP 3000™, AP 8000™, and AP 9000S™ designations (available from (DuPont Electronics & Industrial, Marlborough, Massachusetts).

The photoresist composition may be coated on the substrate by any suitable method, including spin coating, spray coating, dip coating, doctor blading, or the like. For example, applying the layer of photoresist may be accomplished by spin coating the photoresist in solvent using a coating track, in which the photoresist is dispensed on a spinning wafer. During dispensing, the wafer is typically spun at a speed of up to 4,000 rotations per minute (rpm), for example, from 200 to 3,000 rpm, for example, 1,000 to 2,500 rpm, for a period from 15 to 120 seconds to obtain a layer of the photoresist composition on the substrate. It will be appreciated by those skilled in the art that the thickness of the coated layer may be adjusted by changing the spin speed and/or the total solids of the composition. A photoresist composition layer formed from the compositions of the invention typically has a dried layer thickness from 3 to 30 micrometers (μm), preferably from greater than 5 to 30 μm, and more preferably from 6 to 25 μm.

The photoresist composition is typically next soft-baked to minimize the solvent content in the layer, thereby forming a tack-free coating and improving adhesion of the layer to the substrate. The soft bake is performed, for example, on a hotplate or in an oven, with a hotplate being typical. The soft bake temperature and time will depend, for example, on the photoresist composition and thickness. The soft bake temperature is typically from 80 to 170° C., and more typically from 90 to 150° C. The soft bake time is typically from 10 seconds to 20 minutes, more typically from 1 minute to 10 minutes, and still more typically from 1 minute to 2 minutes. The heating time can be readily determined by one of ordinary skill in the art based on the ingredients of the composition.

The photoresist layer is next pattern-wise exposed to activating radiation to create a difference in solubility between exposed and unexposed regions. Reference herein to exposing a photoresist composition to radiation that is activating for the composition indicates that the radiation can form a latent image in the photoresist composition. The exposure is typically conducted through a patterned photomask that has optically transparent and optically opaque regions corresponding to regions of the resist layer to be exposed and unexposed, respectively. Such exposure may, alternatively, be conducted without a photomask in a direct writing method, typically used for e-beam lithography. The activating radiation typically has a wavelength of sub-400 nm, sub-300 nm or sub-200 nm, with wavelengths of 248 nm (KrF), 193 nm (ArF), or 13.5 nm (EUV) being preferred, or e-beam lithography also being preferred. Preferably, the activating radiation is at a wavelength of 248 nm. The methods find use in immersion or dry (non-immersion) lithography techniques. The exposure energy is typically from 1 to 200 millijoules per square centimeter ($mJ/cm^2$), preferably from 10 to 100 $mJ/cm^2$, and more preferably from 20 to 50 $mJ/cm^2$, dependent upon the photoresist composition.

Following exposure of the photoresist layer to activating radiation, a post-exposure bake (PEB) or heating step is performed on the exposed photoresist layer. The PEB can be conducted, for example, on a hotplate or in an oven, with a hotplate being typical. Conditions for the PEB will depend, for example, on the photoresist composition and the thickness of the layers. The PEB is typically conducted at a temperature from 70 to 150° C., preferably from 75 to 120° C., and for a time from 30 to 120 seconds. A latent image defined by the polarity-switched (exposed regions) and unswitched regions (unexposed regions) is formed in the photoresist.

The exposed photoresist layer is then developed with a suitable developer to selectively remove those regions of the layer that are soluble in the developer while the remaining insoluble regions form the resulting photoresist pattern. In a positive tone development (PTD) process, the exposed regions of the photoresist layer are removed during development and the unexposed regions of the photoresist layer remain after development. Conversely, in a negative tone development (NTD) process, the unexposed regions of the photoresist layer are removed during development and the exposed regions of the photoresist layer remain after development. Application of the developer may be accomplished by any suitable method such as described above with respect to application of the photoresist composition, with spin coating being typical. The development time is for a period effective to remove the soluble regions of the photoresist, with a time of from 5 to 60 seconds being typical. Development is typically conducted at room temperature.

Suitable PTD developers for a PTD process include aqueous base developers, for example, quaternary ammonium hydroxide solutions such as tetramethylammonium hydroxide (TMAH), preferably 0.26 normal (N) TMAH, tetraethylammonium hydroxide, tetrabutylammonium hydroxide, sodium hydroxide, potassium hydroxide, sodium carbonate, potassium carbonate, or the like. Suitable NTD developers for an NTD process include organic solvents, with the cumulative content of organic solvents in the NTD developer in an amount of 50 wt % or greater, typically 95 wt % or greater, 98 wt % or greater, or 100 wt %, based on etching. The photoresist pattern may, for example, be used for pattern transfer to an underlying hardmask layer which, in turn, is used as an etch mask for pattern transfer to one or more layers below the hardmask layer. If the photoresist pattern is not consumed during pattern transfer, it may be removed from the substrate by known techniques, for example, oxygen plasma ashing. The photoresist compositions may, when used in one or more such patterning processes, be used to fabricate semiconductor devices such as memory devices, processor chips (CPUs), graphics chips, optoelectronic chips, LEDs, OLEDs, as well as other electronic devices.

The invention is further illustrated by the following non-limiting examples.

EXAMPLES

Synthesis of MD1

The synthetic scheme for the monomer designated MD1 is shown in Scheme 1.

Scheme 1

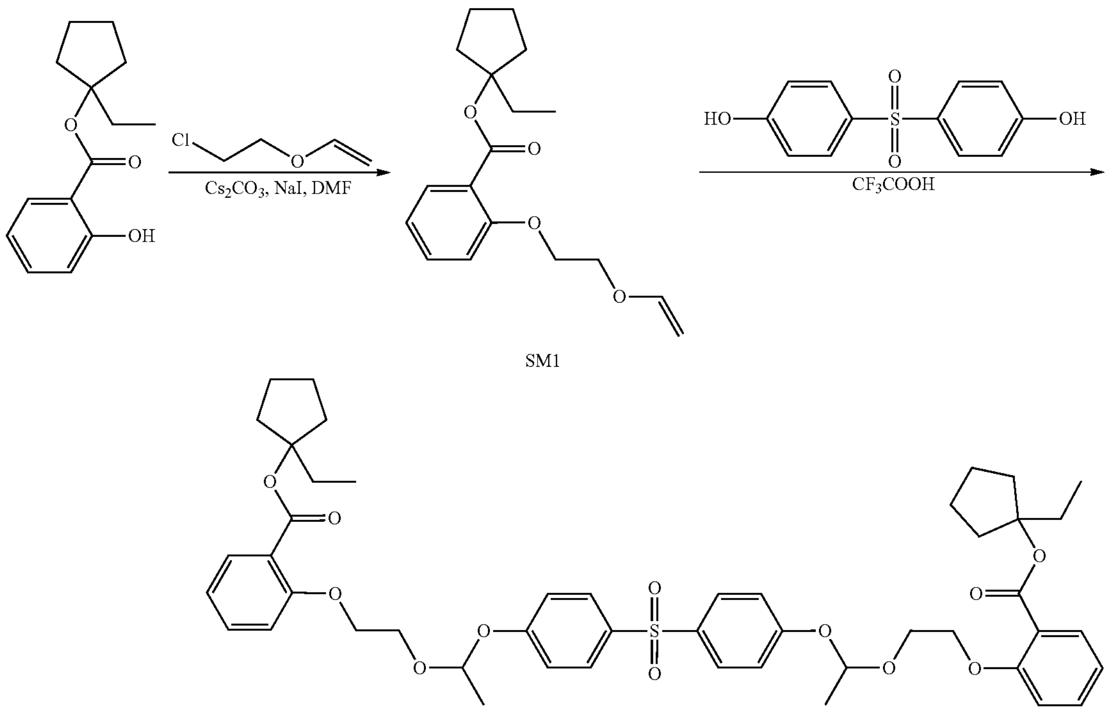

SM1

MD1 total weight of the developer. Suitable organic solvents for the NTD developer include, for example, those chosen from ketones, esters, ethers, hydrocarbons, and mixtures thereof. The developer is typically 2-heptanone or n-butyl acetate.

A coated substrate may be formed from the photoresist compositions of the invention. Such a coated substrate includes: (a) a substrate having one or more layers to be patterned on a surface thereof; and (b) a layer of the photoresist composition over the one or more layers to be patterned.

The photoresist pattern may be used, for example, as an etch mask, thereby allowing the pattern to be transferred to one or more sequentially underlying layers by known etching techniques, typically by dry-etching such as reactive ion In a reaction vessel, 1-ethylcyclopentyl-2-hydroxybenzoate (30.0 grams (g), 128.2 millimoles (mmol)) was suspended in N,N-dimethylformamide (DMF) to achieve a 6 wt % solution. Cesium carbonate (83.5 g, 256.4 mmol) and sodium iodide (1.92 g, 12.82 mmol) were added neatly to the solution to form a reaction mixture. Next, (2-chloroethoxy) ethene (16.4 g, 153.8 mmol) was added slowly and dropwise to the reaction mixture while stirring. The resulting reaction mixture was heated to an internal temperature of 70° C. for 18 hours. The reaction mixture was then allowed to cool to room temperature and was diluted with deionized (DI) water (1.5 liters (L)), and the aqueous mixture was extracted with methyl tert-butyl ether (3x300 mL). The organic layers were combined and washed with DI water (5x200 mL), and the solvents were removed under a reduced pressure to afford intermediate SM1 as a colorless oil (37.0 g, yield of 95%).

Proton nuclear magnetic resonance spectroscopy ($^1$H-NMR) (500 MHz, chloroform-d) chemical shift (6, parts per million (ppm)): 7.72 (dd, 1H, ArH), 7.42 (ddd, 1H, ArH), 7.00 (td, 1H, ArH), 6.97 (d, 1H, ArH), 6.55 (dd, 1H, alkenyl-H), 4.31-4.21 (m, 3H, $CH_2$/alkenyl-H), 4.12-4.03 (m, 3H, $CH_2$/alkenyl-H), 2.33-2.24 (m, 2H, $CH_2$), 2.14 (q, 2H, $CH_2$), 1.86-1.71 (m, 4H, $CH_2$), 1.69-1.56 (m, 2H, $CH_2$), 0.96 (t, 3H, $CH_3$).

A reaction vessel was charged with 4,4'-sulfonyldiphenol (2.00 g, 8.0 mmol) and propylene glycol monomethyl ether acetate (PGMEA) to provide a 20 wt % solution. Traces of water were removed by azeotropic distillation. Trifluoroacetic acid (0.02 g, 0.2 mmol) and vinyl ether monomer intermediate SM1 (4.99 g, 16.4 mmol) were added to the anhydrous solution to provide a reaction mixture. The reaction mixture was stirred at room temperature (ca. 23° C.) for 24 hours. The reaction solution was then passed through an alumina column and the solvent was removed under a reduced pressure to provide MD1 (5.58 g, yield of 80.0%).

$^1$H-NMR (acetone-$d_6$), δ (ppm): 7.88 (d, 4H, ArH), 7.24 (d, 4H, ArH), 7.64 (d, 2H, ArH), 7.43 (m, 2H, ArH), 7.07 (d, 2H, ArH), 7.00 (m, 2H, ArH), 5.82 (q, 2H, CH), 4.07 (m, 4H, $CH_2$), 3.93 (m, 4H, $CH_2$), 2.25 (m, 4H, $CH_2$), 2.10 (m, 4H, $CH_2$) 1.84-1.59 (m, 12H, $3CH_2$), 1.51 (d, 6H, $CH_3$), and 0.92 (t, 6H, $CH_3$).

Synthesis of MD2

The synthetic scheme for the monomer designated MD2 is shown in Scheme 2.

In a reaction vessel, 1-ethylcyclopentyl-2-hydroxy-5-iodobenzoate (36.0 g, 100 mmol) was suspended in DMF to achieve a 9 wt % solution. Cesium carbonate (65.1 g, 200 mmol) and sodium iodide (1.50 g, 10 mmol) were added neatly to the solution to form a reaction mixture. Then (2-chloroethoxy)ethene (12.8 g, 120 mmol) was added slowly and dropwise to the reaction mixture while stirring. The reaction mixture was heated to an internal temperature of 70° C. for 4 hours. Then, (2-chloroethoxy)ethene (10.7 g, 100 mmol) was added to the reaction mixture, and the reaction mixture was heated at 70° C. for an additional 14 hours. The reaction mixture was allowed to cool to room temperature and then was diluted with DI water (1.5 L), and the aqueous mixture was extracted with methyl tert-butyl ether (3×250 mL). The organic layers were combined and washed with water (5×200 mL), and the solvents were removed under a reduced pressure to afford the vinyl ether monomer intermediate SM2 as a colorless oil (37.5 g, yield of 87%).

$^1$H-NMR (500 MHz, chloroform-d) δ (ppm): 7.94 (d, 1H, ArH), 7.66 (dd, 1H, ArH), 6.73 (d, 1H, ArH), 6.51 (dd, 1H, alkenyl-H), 4.27-4.18 (m, 3H, $CH_2$/alkenyl-H), 4.08-4.00 (m, 3H, $CH_2$/alkenyl-H), 2.29-2.18 (m, 2H, $CH_2$), 2.09 (q, 2H, $CH_2$), 1.82-1.68 (m, 4H, $CH_2$), 1.67-1.57 (m, 2H, $CH_2$), 0.93 (t, 3H, $CH_3$).

A reaction vessel was charged with 4,4'-sulfonyldiphenol (2.00 g, 8.0 mmol) and PGMEA to provide a 35 wt % solution. Traces of water were removed by azeotropic distillation. Trifluoroacetic acid (0.02 g, 0.2 mmol) and vinyl ether monomer intermediate SM2 (7.83 g, 16.4 mmol) were Scheme 2

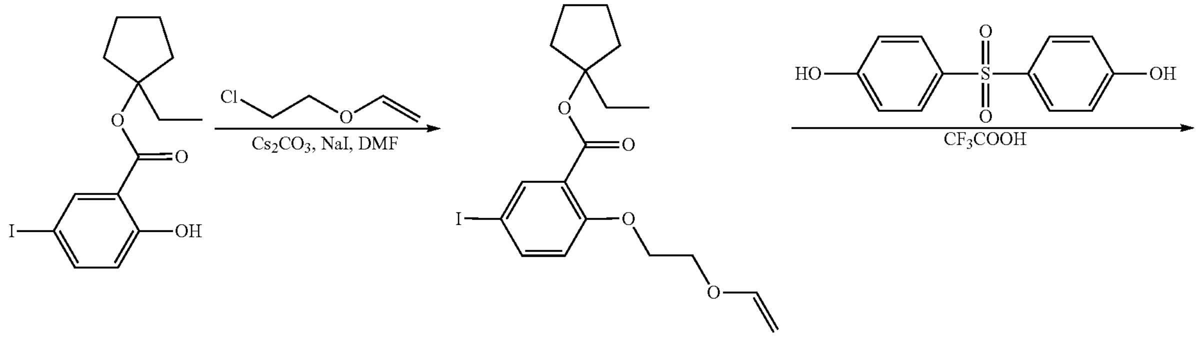

SM2

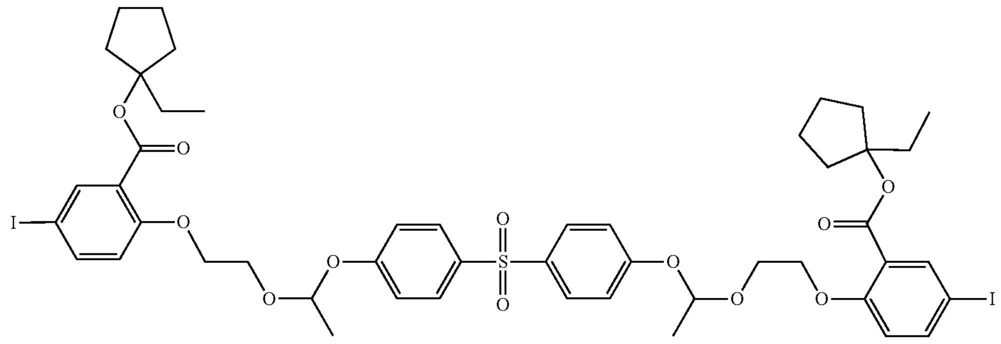

MD2 added to the anhydrous solution to provide a reaction mixture. The reaction mixture was stirred at room temperature (ca. 23° C.) for 24 hours. The reaction mixture was then passed through an alumina column and the solvent was removed under a reduced pressure to provide MD2 (7.43 g, yield of 75.7%).

$^1$H-NMR (acetone-$d_6$), δ (ppm): 7.89 (d, 4H, ArH), 7.87 (s, 2H, ArH), 7.75 (d, 2H, ArH), 7.24 (d, 4H, ArH), 6.95 (d, 2H, ArH), 5.77 (q, 2H, CH), 4.06 (m, 4H, $CH_2$), 3.89 (m, 4H, $CH_2$), 2.23 (m, 4H, $CH_2$), 2.09 (m, 4H, $CH_2$) 1.84-1.59 (m, 12H, $3CH_2$), 1.51 (d, 6H, $CH_3$), and 0.92 (t, 6H, $CH_3$).

Synthesis of MD3

The synthetic scheme for the monomer designated MD3 is shown in Scheme 3.

(5×200 mL), and the solvents were removed under a reduced pressure to afford intermediate SM3 as a colorless oil (37.5 g, yield of 90%).

$^1$H-NMR (500 MHz, chloroform-d) δ (ppm): 8.20 (d, 1H, ArH), 7.92 (d, 1H, ArH), 6.52 (dd, 1H, alkenyl-H), 4.30-4.20 (m, 3H, $CH_2$/alkenyl-H), 4.10 (t, 2H, $CH_2$), 4.05 (dd, 1H, alkenyl-H), 2.28-2.15 (m, 2H, $CH_2$), 2.10 (q, 2H, $CH_2$), 1.84-1.71 (m, 4H, $CH_2$), 1.70-1.60 (m, 2H, $CH_2$), 0.93 (t, 3H, $CH_3$).

A reaction vessel was charged with 4,4'-(perfluoropropane-2,2-diyl)diphenol (2.00 g, 5.9 mmol) and PGMEA to provide a 35 wt % solution. Traces of water were removed by azeotropic distillation. Trifluoroacetic acid (0.02 g, 0.2 mmol) and vinyl ether monomer intermediate SM3 (7.14 g, Scheme 3

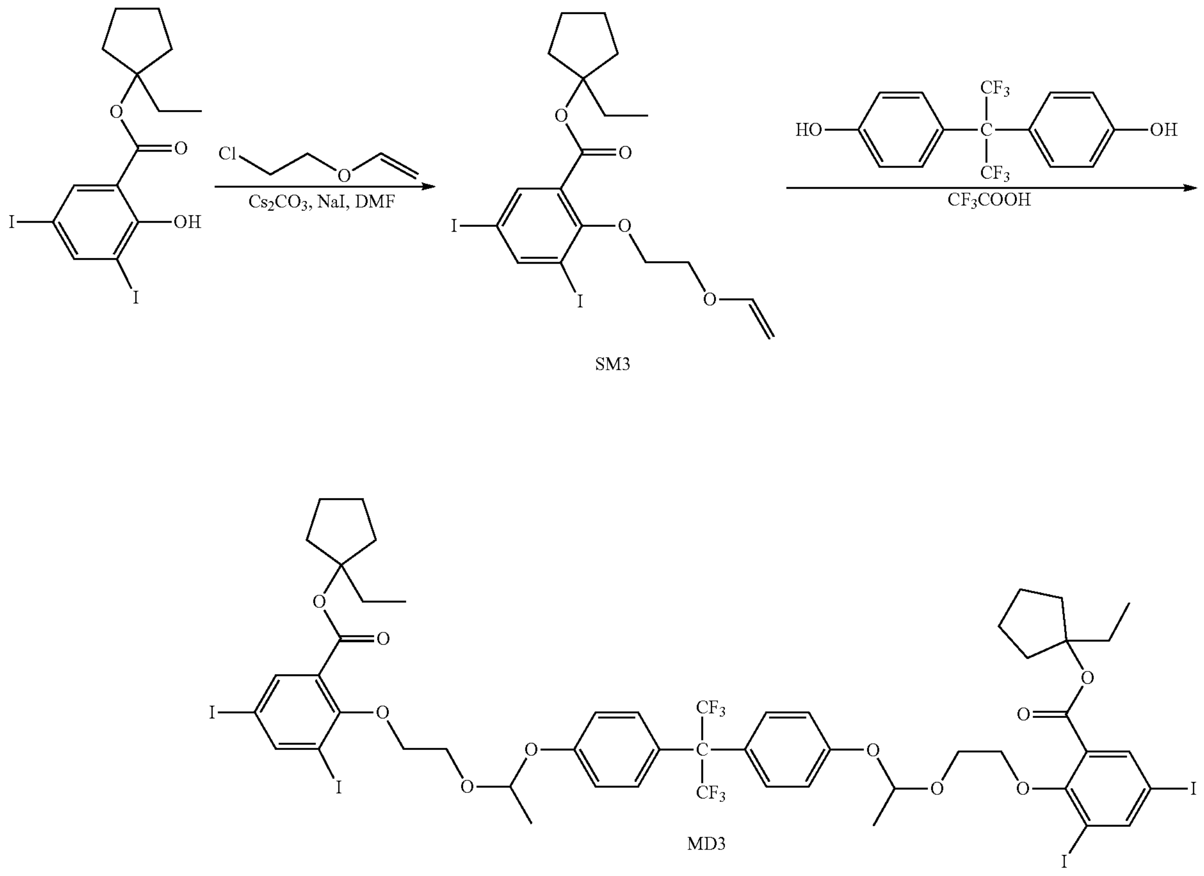

SM3

MD3

In a reaction vessel, 1-ethylcyclopentyl-1-hydroxy-3,5-diiodobenzoate (36.5 g, 75 mmol) was suspended in DMF to achieve a 12 wt % solution. Cesium carbonate (48.9 g, 150 mmol) and sodium iodide (1.12 g, 7.5 mmol) were added neatly to form a reaction mixture. Then, (2-chloroethoxy) ethene (12.8 g, 120 mmol) was added slowly added dropwise to the reaction mixture while stirring. The reaction mixture was heated to an internal temperature of 70° C. for 16 hours. Then, additional (2-chloroethoxy)ethene (9.6 g, 100 mmol) was added to the reaction mixture, and the reaction temperature was increased to 85° C. for 1 hour. The reaction mixture was allowed to cool to room temperature and was then diluted with DI water (1.5 L), and the aqueous mixture was extracted with ethyl acetate (4×200 mL). The organic layers were combined and washed with DI water 12.2 mmol) were added to the anhydrous solution to provide a reaction mixture. The reaction mixture was stirred at room temperature (ca. 23° C.) for 24 hours. The reaction mixture was then passed through an alumina column and the solvent was removed under a reduced pressure to provide MD3 (7.2 g, yield of 79.0%).

$^1$H-NMR (acetone-$d_6$), δ (ppm): 8.36 (s, 2H, ArH), 8.22 (s, 2H, ArH), 7.33 (d, 4H, ArH), 7.13 (d, 4H, ArH), 5.69 (q, 2H, CH), 4.14 (m, 4H, $CH_2$), 4.01 (m, 4H, $CH_2$), 2.20 (m, 4H, $CH_2$), 2.09 (m, 4H, $CH_2$) 1.84-1.59 (m, 12H, $CH_2$), 1.54 (d, 6H, $CH_3$), and 0.93 (t, 6H, $CH_3$).

Synthesis of MD4

The synthetic scheme for the monomer designated MD4 is shown in Scheme 4.

Scheme 4

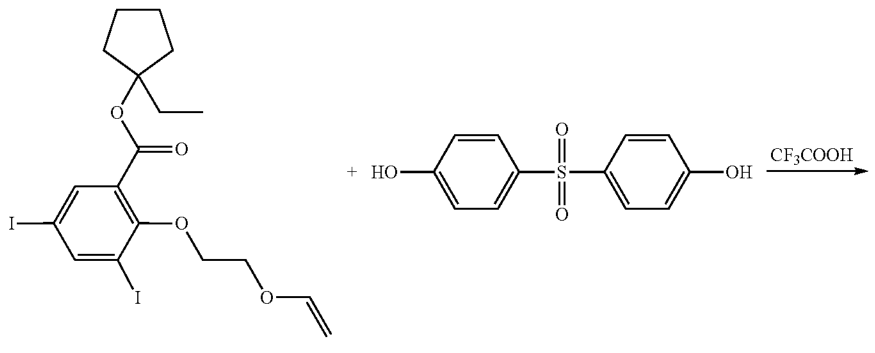

SM3

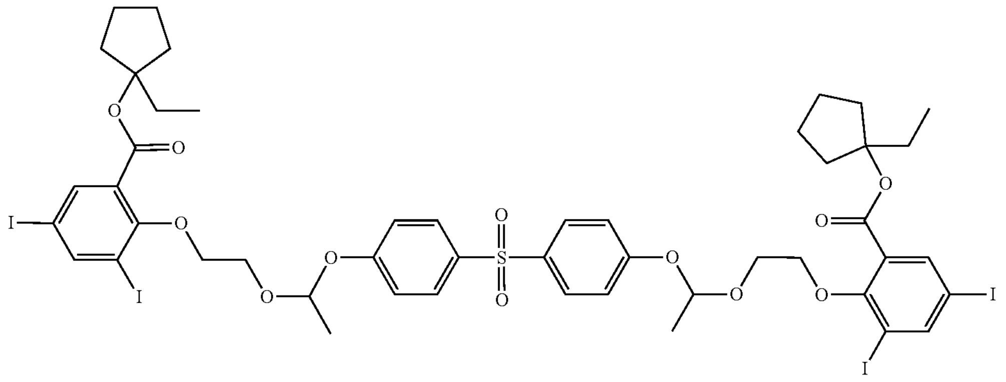

MD4

A reaction vessel was charged with 4,4'-sulfonyldiphenol (2.00 g, 8.0 mmol) and PGMEA to provide a 35 wt % solution. Traces of water were removed by azeotropic distillation. Trifluoroacetic acid (0.02 g, 0.2 mmol) and vinyl ether monomer intermediate SM3 (9.59 g, 16.4 mmol) were added to the anhydrous solution to provide a reaction mixture. The reaction mixture was stirred at room temperature (ca. 23° C.) for 24 hours. The reaction mixture was then passed through an alumina column and the solvent was removed under a reduced pressure to provide MD4 (8.3 g, yield of 71.7%).

$^1$H-NMR (acetone-$d_6$), δ (ppm): 8.29 (d, 2H, ArH), 7.96 (d, 2H, ArH), 7.89 (d, 4H, ArH), 7.24 (d, 4H, ArH), 5.77 (q, 2H, CH), 4.09 (m, 4H, $CH_2$), 3.96 (m, 4H, $CH_2$), 2.20 (m, 4H, $CH_2$), 2.09 (m, 4H, $CH_2$) 1.84-1.59 (m, 12H, $CH_2$), 1.51 (d, 6H, $CH_3$), and 0.92 (t, 6H, $CH_3$).

Synthesis of MD5

The synthetic scheme for the monomer designated MD5 is shown in Scheme 5.

Scheme 5

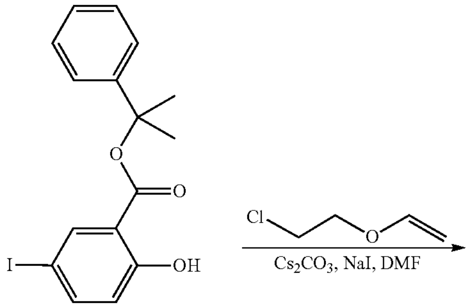

-continued

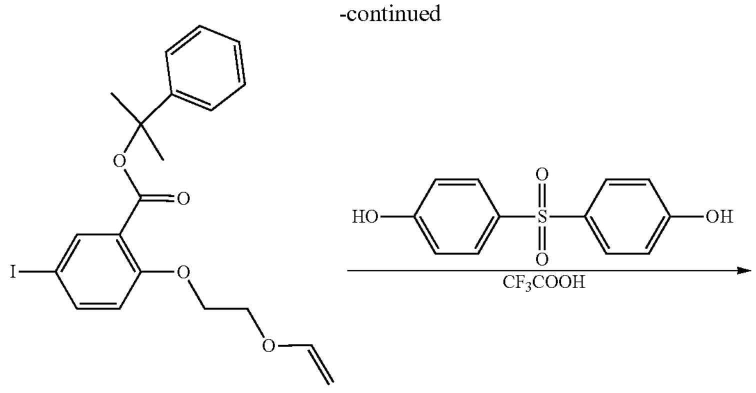

SM4

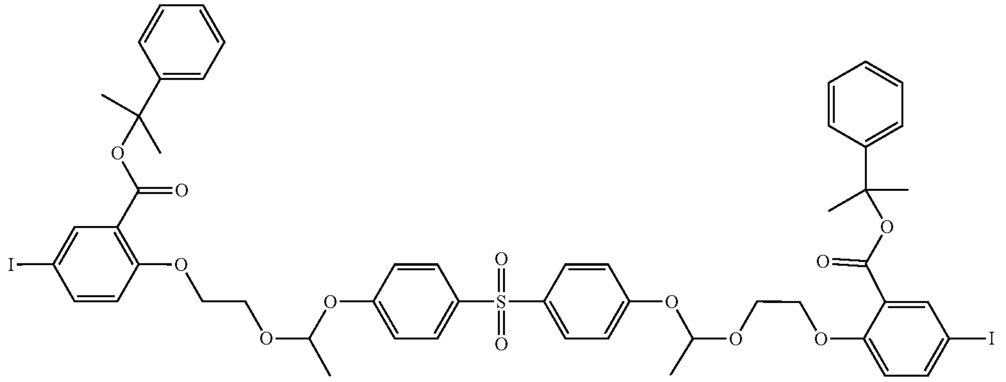

MD5

In a reaction vessel, 2-phenylpropan-2-yl 2-hydroxy-5-iodobenzoate (11.5 g, 30 mmol) was suspended in DMP to achieve a 11.5 wt % solution. Cesium carbonate (19.5 g, 60 mmol) and sodium iodide (0.5 g, 3 mmol) were added neatly to the solution to form a reaction mixture. The, (2-chloroethoxy)ethene (3.8 g, 36 mmol) was added slowly and dropwise to the reaction mixture while stirring. The reaction mixture was heated to an internal temperature of 70° C. for 4 hours. Then, an additional (2-chloroethoxy)ethene (3.2 g, 30 mmol) was added to the reaction mixture, and the reaction mixture was heated at 70° C. for an additional 16 hours. The reaction mixture was allowed to cool to room temperature and then diluted with DI water (1.0 L), and the aqueous mixture was extracted with ethyl acetate (3×100 mL). The organic layers were combined and washed with DI water (5×100 mL), and the solvents were removed under a reduced pressure to afford intermediate SM4 as a colorless oil (11.1 g, yield of 82%).

$^1$H-NMR (500 MHz, acetone-$d_6$) δ (ppm): 7.90 (s, 1H, ArH), 7.79 (d, 1H, ArH), 7.53 (d, 2H, ArH), 7.34 (t, 2H, ArH), 7.23 (t, 1H, ArH), 7.00 (d, 1H, ArH), 6.57 (dd, 1H, alkenyl-H), 4.34 (t, 2H, $CH_2$), 4.27 (d, 1H, alkenyl-H), 4.13 (t, 2H, $CH_2$), 4.01 (d, 1H, alkenyl-H), 1.86 (s, 6H, $CH_3$).

A reaction vessel was charged with 4,4'-sulfonyldiphenol (2.00 g, 8.0 mmol) and PGMEA to provide a 35 wt % solution. Traces of water were removed by azeotropic distillation. Trifluoroacetic acid (0.02 g, 0.2 mmol) and vinyl ether monomer intermediate SM4 (6.17 g, 12.3 mmol) were added to the anhydrous solution to provide a reaction mixture. The reaction mixture was stirred at room temperature (ca. 23° C.) for 24 hours. The reaction mixture was then passed through an alumina column and the solvent was removed under a reduced pressure to provide MD5 (6.9 g, yield of 72.0%).

$^1$H-NMR (acetone-$d_6$), δ (ppm): 7.96 (t, 2H, ArH), 7.84 (d, 4H, ArH), 7.78 (dt, 2H, ArH), 7.53 (d, 4H, ArH), 7.33 (t, 4H, ArH), 7.23 (t, 2H, ArH), 7.15 (d, 4H, ArH), 6.96 (d, 2H, ArH), 5.75 (q, 2H, CH), 4.08 (m, 4H, $CH_2$), 3.92 (m, 4H, $CH_2$), 1.86 (d, 12H, $CH_3$), and 1.45 (d, 6H, $CH_3$).

Synthesis of C1

The synthetic scheme for the monomer designated $C_1$ is shown in Scheme 6.

Scheme 6

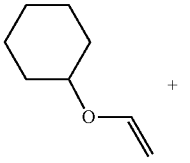

SC1

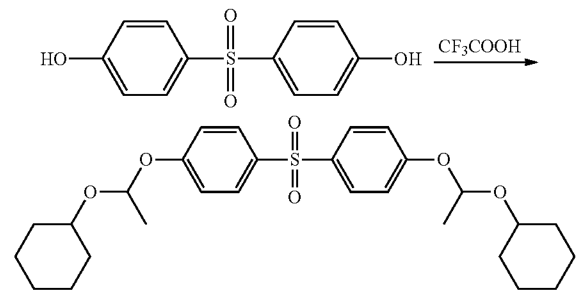

C1

A reaction vessel was charged with 4,4'-sulfonyldiphenol (10.0 g, 40.0 mmol) and PGMEA to provide a 20 wt % solution. Traces of water were removed by azeotropic distillation. Trifluoroacetic acid (0.11 g, 0.98 mmol) and vinyl ether SC1 (10.34 g, 81.9 mmol) were added to the solution to provide a reaction mixture. The reaction mixture was stirred at room temperature for 24 hours. The reaction mixture was then passed through an alumina column and the solvent was removed under a reduced pressure to provide C1 (15.4 g in 76.0% yield).

$^1H$-NMR (acetone-$d_6$), δ: 7.91 (d, 4H, ArH), 7.18 (d, 4H, ArH), 5.72 (q, 2H, CH), 3.26 (m, 2H, CH), 1.82 (m, 2H, $CH_2$), 1.68 (m, 2H, $CH_2$), 1.47 (d, 6H, $CH_3$), and 1.90-1.20 (m, 12H, $CH_2$).

Synthesis of Polymer P1

Polymer P1 was prepared from the monomers MA1, MB1, and MC1, at a molar ratio of 45/45/10. A monomer feed solution was prepared by dissolving MA1 (35.3 g, 218 mmol), MB1 (44.5 g, 218 mmol), and MCi (24.2 g, 48 mmol) in 104 g of PGMEA. An initiator solution was separately prepared by dissolving 6.6 g (26.6 mmol) of dimethyl 2,2'-azobis(2-methylpropionate) (obtained as V-65 from Wako Pure Chemical Industries, Ltd.) in 19.8 g of PGMEA/tetrahydrofuran (THF) (1:1 by wt %).

MA1

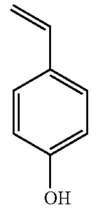

MB1

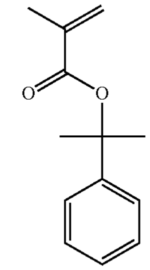

MC1

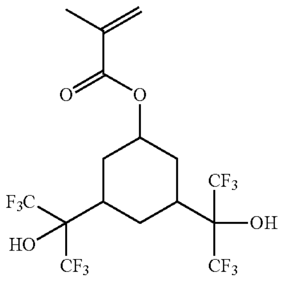

The polymerization was performed in a 3-neck round bottom flask fitted with a water condenser and a thermometer to monitor the reaction in the flask. The flask was charged with 53.3 g of PGMEA and heated to 75° C. The monomer feed solution and the initiator solution were each delivered to the flask using syringe pumps over 4 hours. The contents of the reaction mixture were then stirred for an additional 2 hours after the additions were completed. The contents were subsequently cooled to room temperature, diluted with 40 g of THF, and precipitated into 3 L of a 7:3 (v/v) mixture of heptane and isopropanol. The resulting reaction product was isolated by filtration and dried overnight at 35° C. under a reduced pressure. The solid product was then dissolved in methanol and combined with a solution of sodium methoxide in methanol. The reaction mixture was heated to 67° C. for 4 hours. The reaction was then allowed to cool to room temperature and pH was neutralized with the addition of acidic resin. The polymer solution was precipitated into deionized (DI) water and the product was dried under a reduced pressure at 35° C. to isolate polymer P1 as a white solid (62 g, Mw=8.5 kg/mol, PDI=1.55).

Photoresist Compositions and Evaluations

Example 1

Photoresist compositions were prepared by combining the components indicated in Table 1, where the amounts are expressed in weight percent (wt %) based on 100 wt % of total non-solvent component. The total solids content for the photoresist compositions was 1.55 wt %. The photoresist compositions were prepared in a solvent mixture of PGMEA and methyl-2-hydroxyisobutryate in a weight ratio of 1:1.

The photoresist compositions were evaluated for line/space (l/s) patterning under KrF exposure using a bright field mask pattern. The photoresist compositions were shaken on a mechanical shaker and then filtered through a PTFE disk-shaped filter having a 0.2-micron pore size. 200 mm silicon wafers overcoated with a BARC stack with 60 nm-thickness AR3™ antireflectant over an 80 nm-thickness AR40A™ antireflectant (DuPont Electronics & Industrial) were each spin-coated with a respective photoresist composition on a TEL Clean Track ACT 8 wafer track and softbaked at 110° C. for 60 seconds to provide a photoresist layer with a target thickness of about 40 nm. The wafers were each exposed with 248 nm radiation on a Canon FPA-5000 ES4 scanner (NA=0.8, outer sigma=0.85, inner sigma=0.57) using a mask having 120 nm 1/s patterns. The wafers were post-exposure baked at 100° C. for 60 seconds, developed with MF-CD26™ TMAH developer (DuPont Electronics & Industrial) for 60 seconds, rinsed with DI water, and dried. Critical dimension (CD) measurements of the formed 1/s patterns were made with a Hitachi S-9380 CD-SEM. Sizing energy ($E_{size}$), and LWR (nm) of the lines were determined based on the CD measurements. Sizing energy is the irradiation energy at which the target 120 nm 1/s pattern was resolved. The results are shown in Table 1.

TABLE 1

| Photoresist Composition | Polymer | PAG | Quencher | Additive Compound | $E_{size}$ (mJ/cm$^2$) | LWR (nm) |
|---|---|---|---|---|---|---|
| PR-1 | P1 (71.82%) | PAG-1 (17.96%) | Q1 (7.18%) | MD1 (3.04%) | 85.9 | 8.76 |
| PR-2 | P1 (71.82%) | PAG-1 (17.96%) | Q1 (7.18%) | MD2 (3.04%) | 90.8 | 9.72 |
| PR-3 | P1 (71.82%) | PAG-1 (17.96%) | Q1 (7.18%) | MD3 (3.04%) | 95.0 | 9.40 |
| PR-4 | P1 (71.82%) | PAG-1 (17.96%) | Q1 (7.18%) | MD4 (3.04%) | 95.5 | 9.82 |
| PR-5 | P1 (71.82%) | PAG-1 (17.96%) | Q1 (7.18%) | MD5 (3.04%) | 94.8 | 8.88 |
| PR-6* | PI (77.38%) | PAG-1 (19.35%) | Q1 (3.27%) | None | 96.6 | 10.87 |
| PR-7* | P1 (71.82%) | PAG-1 (17.96%) | Q1 (7.18%) | C1 (3.04%) | 91.7 | 10.28 |

*denotes a comparative photoresist composition

The structures of the PAG (PAG-1) and the quencher (Q1) were as follows:

PAG-1

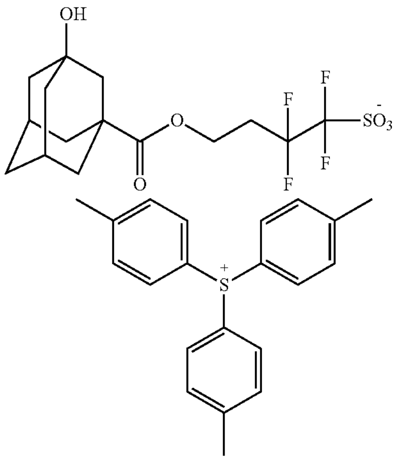

Q1

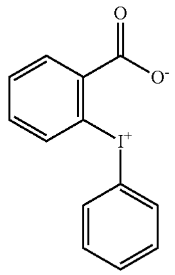

As shown above in Table 1, the inventive photoresist compositions PR-1 to PR-5 achieved improved LWR (a decreased LWR value) relative to comparative photoresist compositions PR-6* and PR-7*.

Example 2

Photoresist compositions were prepared by combining the components indicated in Table 2, where the amounts are expressed in wt % based on 100 wt % of total non-solvent component. The total solids content for the photoresist compositions was 1.55 wt %. The photoresist compositions were prepared in a solvent mixture of PGMEA and methyl-2-hydroxyisobutyrate in a weight ratio of 1:1.

The photoresist compositions of Table 2 were evaluated for trench (TR) patterning under KrF exposure as described above and using a dark field mask pattern. $E_{size}$ and LWR of the spaces were determined based on the CD measurements. Sizing energy was determined from the irradiation energy at which the target 120 nm TR pattern was resolved. The results are shown in Table 2.

TABLE 2

| Photo-resist Com-position | Polymer | PAG | Quencher | Additive | $E_{size}$ (mJ/cm$^2$) | LWR (nm) |
|---|---|---|---|---|---|---|
| PR-8 | P1 (71.82%) | PAG-1 (17.96%) | Q1 (7.18%) | MD1 (3.04%) | 87.25 | 9.16 |
| PR-9 | P1 (71.82%) | PAG-1 (17.96%) | Q1 (7.18%) | MD2 (3.04%) | 92.04 | 10.16 |

TABLE 2-continued

| Photo-resist Com-position | Polymer | PAG | Quencher | Additive | $E_{size}$ (mJ/cm$^2$) | LWR (nm) |
|---|---|---|---|---|---|---|
| PR-10 | P1 (71.82%) | PAG-1 (17.96%) | Q1 (7.18%) | MD3 (3.04%) | 96.53 | 9.28 |
| PR-11 | P1 (71.82%) | PAG-1 (17.96%) | Q1 (7.18%) | MD4 (3.04%) | 96.86 | 9.91 |
| PR-12 | P1 (71.82%) | PAG-1 (17.96%) | Q1 (7.18%) | MD5 (3.04%) | 96.64 | 9.1 |
| PR-13* | P1 (77.38%) | PAG-1 (19.35%) | Q1 (3.27%) | None | 97.22 | 10.91 |
| PR-14* | P1 (71.82%) | PAG-1 (17.96%) | Q1 (7.18%) | C1 (3.04%) | 92.26 | 10.45 |

*denotes a comparative photoresist composition

As shown above in Table 2, the inventive photoresist compositions PR-8 to PR-12 achieved improved LWR (i.e., a decreased LWR) relative to the comparative photoresist compositions PR-13* to PR-14*.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A compound, represented by Formula (1):

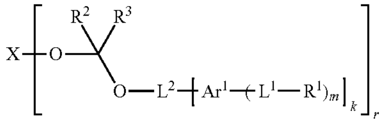

(1)

wherein,

X is represented by one of Formulae (4) to (9):

$$*—Ar^2—*' \quad (4)$$

$$*—Ar^2—O—Ar^3—*' \quad (5)$$

(6)

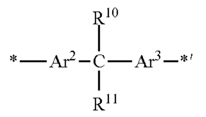

(7)

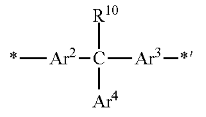

(8)

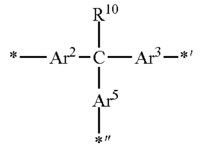

-continued (9)

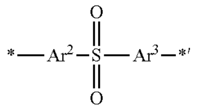

wherein, in Formulae (4) to (9), $Ar^2$, $Ar^3$, and $Ar^5$ are each independently substituted or unsubstituted $C_{6-30}$ arylene or substituted or unsubstituted $C_{3-30}$ heteroarylene;

wherein $Ar^2$ in Formula (4) is monocyclic;

$Ar^4$ is substituted or unsubstituted $C_{6-30}$ aryl or substituted or unsubstituted $C_{3-30}$ heteroaryl;

$R^{10}$ and $R^{11}$ are each independently hydrogen, substituted or unsubstituted $C_{1-30}$ alkyl, substituted or unsubstituted $C_{3-30}$ cycloalkyl, substituted or unsubstituted $C_{1-30}$ heterocycloalkyl, substituted or unsubstituted $C_{6-30}$ aryl, substituted or unsubstituted $C_{7-30}$ arylalkyl, substituted or unsubstituted $C_{7-30}$ alkylaryl, substituted or unsubstituted $C_{6-30}$ aryloxy, substituted or unsubstituted $C_{3-30}$ heteroaryl, substituted or unsubstituted $C_{4-30}$ alkylheteroaryl, substituted or unsubstituted $C_{4-30}$ heteroarylalkyl, or substituted or unsubstituted $C_{3-30}$ heteroaryloxy, and

*, * ' and *" each indicates a point of attachment to a respective adjacent oxygen atom;

each $L^1$ is independently a single bond or a divalent linking group;

each $L^2$ is a single bond or a linking group;

each $Ar^1$ is independently substituted or unsubstituted $C_{6-30}$ arylene or substituted or unsubstituted $C_{3-30}$ heteroarylene, wherein the substituted $C_{6-30}$ arylene and the substituted $C_{3-30}$ heteroarylene are each independently substituted with at least one of halogen, $C_{1-30}$ alkyl, $C_{1-30}$ alkoxy, $C_{4-30}$ cycloalkyl, $C_{3-30}$ heterocycloalkyl, $C_{2-30}$ alkenyl, $C_{2-30}$ alkynyl, $C_{6-30}$ aryl, $C_{7-30}$ arylalkyl, $C_{7-30}$ alkylaryl, $C_{6-30}$ aryloxy, $C_{3-30}$ heteroaryl, $C_{4-30}$ alkylheteroaryl, $C_{4-30}$ heteroarylalkyl, or $C_{3-30}$ heteroaryloxy;

each $R^1$ is independently an organic group comprising an acid-labile group;

$R^2$ and $R^3$ are each independently hydrogen, or substituted or unsubstituted $C_{1-30}$ alkyl;

$R^2$ and $R^3$ together optionally form a ring via a single bond or a divalent linking group, wherein the ring is substituted or unsubstituted;

m is an integer greater than or equal to 1;

k is an integer from 1 to 5;

r is 2 or 3, and wherein the compound is non-polymeric, wherein $R^1$ has a structure represented by one of Formula (2a) or Formula (2b):

(2a)

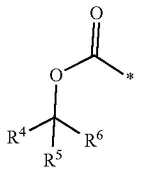

-continued (2b)

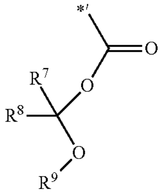

wherein, in Formulae (2a) and (2b), $R^4$ to $R^6$ are each independently hydrogen, substituted or unsubstituted $C_{1-20}$ alkyl, substituted or unsubstituted $C_{3-20}$ cycloalkyl, substituted or unsubstituted $C_{3-20}$ heterocycloalkyl, substituted or unsubstituted $C_{2-20}$ alkenyl, substituted or unsubstituted $C_{3-20}$ cycloalkenyl, substituted or unsubstituted $C_{3-20}$ heterocycloalkenyl, substituted or unsubstituted $C_{6-20}$ aryl, or substituted or unsubstituted $C_{2-20}$ heteroaryl, provided that no more than one selected from $R^4$ to $R^6$ is hydrogen, and provided that if one of $R^4$ to $R^6$ is hydrogen, then at least one of the others from $R^4$ to $R^6$ substituted or unsubstituted $C_{6-20}$ aryl or substituted or unsubstituted $C_{3-20}$ heteroaryl, each of $R^4$ to $R^6$ may optionally further include a divalent linking group as part of its structure, $R^7$ and $R^8$ are each independently hydrogen, substituted or unsubstituted $C_{1-20}$ alkyl, substituted or unsubstituted $C_{3-20}$ cycloalkyl, substituted or unsubstituted $C_{3-20}$ heterocycloalkyl, substituted or unsubstituted $C_{6-20}$ aryl, or substituted or unsubstituted $C_{2-20}$ heteroaryl, each of $R^7$ and $R^8$ may optionally further include a divalent linking group as part of its structure, $R^9$ is substituted or unsubstituted $C_{1-20}$ alkyl, substituted or unsubstituted $C_{3-20}$ cycloalkyl, substituted or unsubstituted $C_{3-20}$ heterocycloalkyl, substituted or unsubstituted $C_{6-20}$ aryl, or substituted or unsubstituted $C_{3-20}$ heteroaryl, $R^9$ optionally may further comprise a divalent linking group as part of its structure, any two of $R^4$ to $R^6$ together optionally may form a ring via a single bond or a divalent linking group, wherein the ring is substituted or unsubstituted, $R^7$ and $R^8$ together optionally may form a ring via a single bond or a divalent linking group, wherein the ring is substituted or unsubstituted, any one or more of $R^7$ or $R^8$ together with Ro optionally may form a ring via a single bond or a divalent linking group, wherein the ring is substituted or unsubstituted, and

* and *' each indicate a binding site to $L^1$.

2. The compound of claim 1, wherein $R^1$ comprises an ester group.

3. The compound of claim 1, wherein $R^1$ comprises an acetal or a ketal group.

4. The compound of claim 1, wherein the compound comprises one or more iodine atoms.

5. The compound of claim 1, wherein each subunit represented by the integer r is the same.

6. A photoresist composition, comprising:

the compound of claim 1; and a solvent.

7. A coated substrate, comprising:

(a) a substrate having one or more layers to be patterned on a surface thereof; and (b) a layer of the photoresist composition of claim 6 disposed over the one or more layers to be patterned.

8. The photoresist composition of claim 6, further comprising a polymer.

9. The photoresist composition of claim 8, wherein the polymer is acid-sensitive.

10. The photoresist composition of claim 6, further comprising a photoacid generator.

11. A method for forming a pattern, the method comprising:

applying a layer of the photoresist composition of claim 6 on a substrate to provide a photoresist layer;

pattern-wise exposing the photoresist layer to activating radiation to provide an exposed photoresist layer; and developing the exposed photoresist layer to provide a photoresist pattern.

12. A method for forming a pattern, the method comprising:

applying a layer of the photoresist composition of claim 6 on a substrate to provide a photoresist composition layer;

pattern-wise exposing the photoresist composition layer to activating radiation to provide an exposed photoresist composition layer; and developing the exposed photoresist composition layer to provide a photoresist pattern.

13. The coated substrate of claim 7, wherein $R^1$ comprises an ester group.

14. The coated substrate of claim 7, wherein $R^1$ comprises an acetal or a ketal group.

15. The coated substrate of claim 7, wherein the compound comprises one or more iodine atoms.

16. The coated substrate of claim 7, wherein each subunit represented by the integer r is the same.

17. The compound of claim 1, wherein X is represented by Formula (5).

18. The compound of claim 1, wherein X is represented by Formula (6).

19. The compound of claim 1, wherein X is represented by Formula (9).

20. The compound of claim 1, wherein X is represented by Formula (7) or (8).

* * * * *